United States Patent
Knopp et al.

(10) Patent No.: US 6,726,680 B1
(45) Date of Patent: *Apr. 27, 2004

(54) AUTOMATED LASER WORKSTATION FOR HIGH PRECISION SURGICAL AND INDUSTRIAL INTERVENTIONS

(75) Inventors: Carl F. Knopp, San Mateo, CA (US); William D. Fountain, Fremont, CA (US); Jerzy Orkiszewski, Livermore, CA (US); Michael Persiantsev, Hayward, CA (US); H. Alfred Sklar, San Francisco, CA (US); Jan Wysopal, Livermore, CA (US)

(73) Assignee: Visx, Incorporated, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/543,840

(22) Filed: Apr. 5, 2000

Related U.S. Application Data

(60) Division of application No. 08/523,738, filed on Sep. 5, 1995, now Pat. No. 6,099,522, which is a continuation of application No. 07/843,374, filed on Feb. 27, 1992, now abandoned, and a continuation-in-part of application No. 07/475,657, filed on Feb. 6, 1990, now abandoned, which is a continuation-in-part of application No. 07/307,315, filed on Feb. 6, 1989, now Pat. No. 5,098,426.

(51) Int. Cl.⁷ ............................................... A61F 9/007
(52) U.S. Cl. ............................... 606/12; 606/5; 606/10
(58) Field of Search .......................... 606/4–6, 10–18; 351/204–212

(56) References Cited

U.S. PATENT DOCUMENTS

| | | |
|---|---|---|
| 4,309,998 A | 1/1982 | Aron nee Rosa et al. |
| 4,391,275 A | 7/1983 | Fankhauser et al. |
| 4,443,075 A * | 4/1984 | Crane .......................... 606/18 |
| 4,579,430 A | 4/1986 | Bille |

(List continued on next page.)

OTHER PUBLICATIONS

Bores, L.D. (1991). "Proceedings of Ophthalmic Technologies," SPIE 1423, C.A. Puliafito, ed. pp 28–39.

Crane, H.D. and Steele, C.M. (1985). "Generation–V Dual–Purkinje–image Eyetracker," Applied Optics 24(4):527–537.

Howland, H.C. et al. (1991). *Optical methods for the measurement of anterior chamber depth*, presented at the Noninvasive Assessment of the Visual System Topical Meeting., WC1, p. 222–225.

Jean, B. et al. (1987). "Eye tracking for Image stabilization," Lasers in Ophthalmology 1(4):197–204.

(List continued on next page.)

Primary Examiner—David M. Shay
(74) Attorney, Agent, or Firm—Townsend Townsend & Crew LLP; Mark D. Barrish, Esq.

(57) ABSTRACT

A method, apparatus and system for template-controlled, precision laser interventions is described that greatly improves interventions such as laser microsurgery, particularly ophthalmic surgery, and industrial micromachining. The instrument and system are applicable to those specialties wherein the positioning accuracy of laser lesions is critical, such as whenever precise operations on a target or series of targets subject to movement during the procedure are to be effected. The system includes a user interface, wherein the user can either draw, adjust, or designate particular template patterns overlaid on a live video images of the target (such as the cornea) which are stabilized and produce an apparently stationary display of the target and provide the means for converting the template pattern into a sequence of automatic motion instructions to direct a laser beam to be sequentially applied replicating the designated template pattern into the corresponding surgical or industrial site.

34 Claims, 19 Drawing Sheets

U.S. PATENT DOCUMENTS

| | | | |
|---|---|---|---|
| 4,665,913 A | | 5/1987 | L'Esperance, Jr. |
| 4,669,466 A | | 6/1987 | L'Esperance |
| 4,761,071 A | | 8/1988 | Baron |
| 4,784,135 A | | 11/1988 | Blum et al. |
| 4,836,670 A | * | 6/1989 | Hutchinson ................ 351/210 |
| 4,848,340 A | | 7/1989 | Bille et al. |
| 4,881,808 A | | 11/1989 | Bille et al. |
| 4,901,718 A | | 2/1990 | Bille et al. |
| 4,907,586 A | | 3/1990 | Bille et al. |
| 5,049,147 A | | 9/1991 | Danon |
| 5,054,907 A | | 10/1991 | Sklar et al. |
| 5,062,702 A | | 11/1991 | Bille |
| 5,098,426 A | | 3/1992 | Sklar et al. |
| 5,147,352 A | | 9/1992 | Azema et al. |
| 5,162,641 A | | 11/1992 | Fountain |
| 5,170,193 A | | 12/1992 | McMillan et al. |
| 5,391,165 A | | 2/1995 | Fountain et al. |
| 5,439,462 A | * | 8/1995 | Bille et al. ..................... 606/6 |
| 5,741,245 A | | 4/1998 | Cozean et al. |
| 5,865,832 A | * | 2/1999 | Knopp et al. ................. 606/10 |
| 6,099,522 A | * | 8/2000 | Knopp et al. ................. 606/10 |
| 6,210,401 B1 | * | 4/2001 | Lai ............................. 606/12 |
| 6,299,307 B1 | * | 10/2001 | Oltean et al. .................. 606/5 |
| 6,325,792 B1 | | 12/2001 | Swinger et al. |

OTHER PUBLICATIONS

Nguyen, N. et al. (1989). "Slowed Saccades in the Acquired Immunodeficiency Syndrome," *American Journal of Ophthalmology* 107:356–360.

Varner, J.R. (1974). *Holographic Nondestructive Testing, Academic Press*, New York, 1974, pp. 105.

* cited by examiner

Radial cut with 8 lines at 45 degrees to each other

AUTOMATED LASER WORKSTATION FOR HIGH PRECISION SURGICAL AND INDUSTRIAL INTERVENTIONS

The present application is a divisional patent application of and claims the benefit of priority from U.S. patent application Ser. No. 08/523,738 filed Sep. 5, 1995 (now U.S. Pat. No. 6,099,522); which is a continuation of Ser. No. 07/843,374 filed Feb. 27, 1992 (now abandoned); which is a continuation-in-part of Ser. No. 07/307,315 filed Feb. 6, 1989 (now U.S. Pat. No. 5,098,426); and a continuation-in-part of Ser. No. 07/475,657 filed Feb. 6, 1990 (now abandoned), the full disclosures of which are incorporated herein by reference.

BACKGROUND OF THE INVENTION

The invention relates to methods and apparatus for performing precise laser interventions, and in particular those interventions relevant to improved methods and apparatus for precision laser surgery. In one preferred embodiment, the system of the invention is used for effecting precise laser eye surgery. In other embodiments the invention is applicable to non-surgical diagnostic procedures or non-medical procedures involving precision laser operations, such as industrial processes.

When performing laser interventions, whether in medical surgery, industrial processes, or otherwise, several fundamental considerations are common to most applications and will influence the viability and effectiveness of the invention. To influence the outcome of the intervention, the present invention addresses both the technical innovations involved in an apparatus to facilitate precision laser interventions, and the methods by which a user of such apparatus can achieve a precise result.

The present invention addresses the following considerations: (1) how does the user identify a target for the laser intervention, (2) how does the user obtain information as to the location and other pertinent features of the target and its important surroundings, (3) how does the user lock onto that target so that the user has the assurance he is affecting the intended target, (4) how does the user localize the effect to the target site, (5) how does the user treat a large number of individual targets, whether continuously connected, piecewise connected, or disconnected, (6) how does the user assess the effect of the intervention, (7) how does the user correct errors committed either during the course of the intervention or as a result of previous interventions, (8) how does the user react to changing conditions during the course of the intervention to ensure the desired result, and (9) how is safety ensured consistent with U.S. Food and Drug Agency regulations for medical instruments and good commercial practice guidelines for industrial applications.

Of particular interest are medical interventions such as surgical procedures described by Sklar et al. (U.S. Pat. No. 5,098,426 and U.S. patent application Ser. No. 475,657 (now abandoned), which are incorporated herein by reference. Although many different kinds of surgery fall within the scope of the present invention, attention is drawn to corneal refractive surgery in ophthalmology for the treatment of myopia, hyperopia, and astigmatism.

For corneal refractive surgery, the above nine considerations reduce to the following objectives (in accordance with the present invention described below): (1) identify the location on or in the cornea to be treated, (2) assure that the target is at the desired distance from the apparatus, determine the topography of the cornea, and determine the location of sensitive tissues to be avoided, (3) identify, quantify, and pursue the motion of suitable part of the cornea which can provide a reference landmark that will not be altered as a result of the surgical intervention and, likewise, the depth of variations (for example, distance form the corneal surface to the front objective lens changing due to blood pressure pulses) of the corneal surface with respect to the apparatus such that said motions become transparent to the user of the apparatus, (4) provide a laser beam which can be focused onto the precise locations designated by the user such that peripheral damage is limited to within the tolerable levels both surrounding the target site and along the laser beam path anterior and posterior to the target site, (5) provide a user interface wherein the user can either draw, adjust, or designate particular template patterns overlaid on a live video image of the cornea and provide the means for converting the template pattern into a sequence of automatic motion instructions which will traverse the laser beam to focus sequentially on a number of points in three dimensional space which will in turn replicate the designated template pattern into the corresponding surgical intervention, (6) assure that items (1)–(3) above can be performed continuously during the course of and subsequent to the surgery to monitor the evolution of the pertinent corneal surface and provide a means of accurate comparison between pre-operative and post-operative conditions, (7) ensure that the structural and physiological damage caused by the surgery to the patient is sufficiently small to permit continued interventions on the same eye, (8) automate the interaction between the various components so that their use is transparent to the user and so that sufficiently fast electronics accelerate completion of the surgical intervention within pre-selected error tolerances, and (9) provide dependable, fail-safe safety features of sufficiently short reaction times to prevent any chance of injury to sensitive corneal tissues. With these objectives fulfilled, the speed of surgery will no longer be limited by human perception delay and response times but by the capability of the apparatus to recognize changing patterns and adjust to the new conditions. Equally important, the accuracy of the surgery will not be constrained by the bounds of human dexterity, but by the mechanical resolution, precision, and response of advanced electro-optical and electromechanical systems.

There are substantial number of different functions which the apparatus of the present invention addresses. Each of the complementary and at times competing, functions requires its own technologies and corresponding subassemblies. The present invention describes how these various technologies integrate into a unified workstation to perform specific interventions most efficaciously. For example, for corneal refractive surgery, as per (1) and (2) above, identify the location to be treated on or in the cornea, the surgeon/user would use a combination of video imaging and automated diagnostic devices as described in Sklar et al. (U.S. Pat. No. 5,098,426 and U.S. patent application Ser. No. 475,657 (now abandoned)), depth ranging techniques as described in Fountain (U.S. Pat. No. 5,162,641), surface topographical techniques, as described in Sklar (U.S. Pat. No. 5,054,907) together with signal enhancement techniques for obtaining curvatures and charting the contours of the corneal surface as described by McMillan and Sklar (U.S. Pat. No. 5,170,193), profilimetry methods as disclosed by McMillan et al. (U.S. Pat. No. 5,283,598), image stabilization techniques as described by Fountain (U.S. Pat. No. 5,162,641), which may all be combined using techniques as described by Sklar et al. (U.S. Pat. No. 5,098,426 and U.S. patent application Ser. No. 475,657 (now abandoned)). All of the above listed patent applications and the patent of Fountain (U.S. Pat. No. 5,391,165) are herein incorporated by reference.

Aspects of the above-referenced disclosures are further used to provide means of satisfying the key aspects (3)–(9) noted above, such as verification of target distance from the apparatus, tracking the motion of the cornea in three dimensions, providing a laser whose parameters can be tuned to selectively generate photodisruption of tissues or photocoagulation as desired, automatically targeting and aiming the laser beam to precise locations, and supplying a surgeon/user with a relatively simple means of using the apparatus through a computer interface.

It is well known that visible light, which is passed without significant attenuation through most ophthalmic tissues, can be made to cause a plasma breakdown anywhere within eye tissue whenever the laser pulse can be focused to sufficiently high irradiance and fluence levels to support an avalanche process. The ensuing localized photodisruption is accomplished by using a strongly focused laser beam such that only in the immediate focal zone is the electric field sufficiently strong to cause ionization and nowhere else. By using short pulses of controllably small laser energy, the damage region can be limited in a predictable manner while still guaranteeing the peak power necessary for localized ionization.

Furthermore, was lasers of increasingly higher repetition rate becoming available, the sometimes intricate patterns desired for a given surgical procedure can be accomplished much faster than the capabilities of a surgeon manually to aim and fire recursively. In prior systems and procedures, the surgeon would aim at a target, verify his alignment, and if the target had not moved, then fire the laser. He would then move on to the next target, and repeat the process. Thus, the limiting factor to the duration of the operation under these prior procedures was the surgeon's reaction time while he focused on a target and the patient's movement while the surgeon found his target and reacted to the target recognition by firing the laser. In practice, a surgeon/user can manually observe, identify, move the laser focus to aim, and fire a laser at not more than two shots per second.

By contrast, a key object of the instrument and system of the present invention is to stabilize the motion of the patient by use of an automated target acquisition and tracking system which allows the surgeon to predetermine his firing pattern based on an image which is automatically stabilized over time. The only limitations in time with the system of the present invention relate to the repetition rate of the laser itself, and the ability of the tracking system to successfully stabilize the image to within the requisite error tolerances for safety and efficacy, while providing a means to automatically interrupt laser firing if the target is not found when a pulse is to be fired. Thus, where it would take several hours for a surgeon/user to execute a given number of shots manually (ignoring fatigue factors), only a few minutes would be required to perform the same procedure when automatic verification of focal point position and target tracking are provided within the device.

It is an object of the present invention to accommodate the most demanding tolerances in laser surgery, particularly eye surgery but also for other medical specialties, through a method, apparatus and system for high-precision laser surgery which provides the surgeon "live" video images containing supporting diagnostic information about depth and position at which a surgical laser will be fired. In a computer, the full information content of a given signal is interpreted so as to provide this supporting diagnostic information, and the resulting accuracy achievable is within a few human cells or better.

The system, apparatus and method of the present invention for precision laser surgery, particularly ophthalmic surgery, take a fully integrated approach based on a number of different instrumental functions combined within a single, fully automated unit. For example, previous conventional diagnostic instruments available to the ophthalmic surgeon have included several different apparatus designed to provide the surgeon/user limited measurement information regarding the cornea of the eye, such as the corneoscope, the keratometer, and the pachometer. The corneoscope provides contour levels on the outer surface of the cornea, or corneal epithelial surface, derived, typically, from projected concentric illumination rings. The keratometer gives cross sectional curvatures of the epithelial surface lens of the eye—the corneal epithelium surface. Only one group of points is examined, giving very limited information. Pachometers are used to measure the central axis thicknesses of the cornea and anterior chamber.

The diagnostic functions fulfilled by these devices are instrumental to characterizing the subject tissue in sufficient detail to allow the surgeon/user to perform high precision ophthalmic surgery. Unfortunately, these and other similar instruments require considerable time to operate. Further, their use required near-total immobilization of the eye or, alternatively, the surgeon/user had to be satisfied with inherent inaccuracies; the immobilization methods thus determined the limitations on the accuracy and efficacy of eye surgery. Nor did the different apparatus lend themselves to being combined into one smoothly operating instrument. For all of the above reasons, operation at time scales matched to the actual motions of the tissues targeted for therapy and/or limited by the fastest human response times to those motions ("real time") has not been possible with any of the conventional instruments used to date.

By contrast, the methods and apparatus disclosed herein, aim to incorporate a mapping and topography means for reconstructing the corneal surface shape and thickness across the entire cornea. It is furthermore within the scope of the present invention to provide such global measurements of the corneal refractive power without sacrificing local accuracies and while maintaining sufficient working distance between the eye and the front optical element of the instrument (objective lens), said measurements to be executed on-line within time scales not limited to human response times. Most standard profilometry techniques were judged inadequate per the above requirements, requiring compromises in either accuracies of the computed curvatures (such as, e.g., standard 'k' readings of keratometers), speed and ease of operation (scanning confocal microscopes) or left no working distance for the ophthalmologist (corneoscope and keratoscopes based on "placido disk" illumination patterns). It is therefore a key objective of the present invention to include a new topography assembly that can overcome the limitations of existing instruments while combining, on-line, and in a cost effective manner, many of the functions of conventional diagnostic instruments presently available to the surgeon, as an integral part of a complete surgical laser unit.

In one embodiment of the present invention, the corneal refractive power is measured using a unique projection and profilometry technique coupled with signal enhancement methods for surface reconstruction as disclosed by McMillan and Sklar in U.S. Pat. No. 5,170,193 and further extended in larger corneal cross-sections via techniques described in McMillan et al. in U.S. Pat. No. 5,283,598, both incorporated herein by reference. In another embodiment, digitized slit lamp video images are used to measure the local radii of curvature across the entire corneal surface as well as the thickness of the cornea, with no built-in a-priori assumptions about the corneal shape. Both embodiments of the topography system benefit greatly from the availability of 3-D tracking capability contained within the apparatus. The feature allows elimination of many of the errors and ambiguities that tend to compromise the accuracy of even the best currently available instruments utilizing fine point edge extraction and advanced surface fitting techniques. With the computerized topographic methods of the present invention, surfaces can be reconstructed (and viewed in 3-D) with accuracies that go well beyond the approximate photokeratometric and pachometry readings as advocated by L'Esperance (U.S. Pat. No. 4,669,466), or even the more sophisticated (but complex) corneal mapping methods as disclosed by Bille (U.S. Pat. No. 5,062,702) and Baron (U.S. Pat. No. 4,761,071).

While tissue topography is a necessary diagnostic tool for measuring parameters instrumental to defining templates for the surgery (e.g., refractive power), such instrumentation is not conducive to use during surgery, but rather before and after surgery. Also, the information thus obtained is limited to those parameters characteristic of surface topography (such as radii of curvature of the anterior and/or posterior layers of the cornea or lens). Yet, in many cases, it is desirable to simultaneously image the target area and deposit laser energy at a specific location within the tissue itself. To allow reliable, on-line monitoring of a given surgical procedure, additional mapping and imaging means must therefore be incorporated. The imaging means is intended to record, in three-dimensions, the location of significant features of the tissue to be operated upon, including features located well within the subject tissue. It is therefore another object of the present invention to provide continuously updated video images to be presented to the surgeon/user as the surgery progresses, said images to be produced in a cost effective manner yet compatible with high resolution and high magnification across a large field of view and at sufficiently low illumination levels to prevent any discomfort to the patient.

The imaging system, or the surgical microscope, requires viewing the reflected light form the cornea, which has two components: (a) specular (or mirror) reflection from a smooth surface, which returns the light at an angle opposite the angle of incidence about the normal from the surface and also preserves the polarization of the incident beam, and (b) diffuse reflection, in which light returned from a rough surface or inhomogeneous material is scattered in all directions and loses the polarization of the incident beam. No surface or material is perfectly smooth or rough; thus all reflected light has a specular and a scattered component. In the case of the cornea there is a strong specular reflection from the front surface/tear layer and weak scattered light from the cellular membranes below. Various standard 'specular microscopes' have been used to suppress the front surface reflection. We have chosen a combination of techniques: some aim at observing the combined reflections without differentiating between specular or diffuse signals (for operations at or in immediate proximity to the surface of the cornea); in others the surface is illuminated with polarized light, with the reflected images then microscopically viewed through a crossed polarizer for operation within deeper layers, after selectively filtering the more anterior reflections. A rejection of the polarized component can thus be achieved, greatly enhancing resolution at low enough light levels to prevent any discomfort to the patient. In either embodiment, the imaging system contained within the apparatus of the invention represents a significant improvement over standard "slit lamp" microscopes such as are in use with most ophthalmic laser systems.

Other efforts at imaging the eye, such as performed with Heidelberg Instrument Confocal Microscope, or as described by Bille (U.S. Pat. No. 4,579,430), either do not lend themselves to inclusion as part of an on-line, cost effective, integrated surgical system (for the former), or rely upon scanning techniques which do not capture an image of the eye at a given instant in time (for the latter). The method of the present invention benefits from having an instantaneous full image rather than a scanned image; for full efficacy, the method does, however, require that the targeted area be stabilized with respect to both the imaging and the laser focal region, so as to enhance the accuracy of laser deposition in tandem with the viewing sharpness.

Tracking is therefore considered a critical element of a system designed onto only to diagnose, but also select treatment, position the treatment beam and image the tissue simultaneously with the treatment, while assuring safety at all times. In the case of corneal surgery, movements of the eye must be followed by a tracking system and, suing dedicated microprocessors, at closed-loop refresh speeds surpassing those achievable by unaided human inspection, by at least an order of magnitude. Tracking by following the subject eye tissue, i.e., recognizing new locations of the same tissue and readjusting the imaging system and the surgical laser aim to the new location, assures that the laser, when firing through a prescribed pattern, will not deviate from the pattern an unacceptable distance. In preferred embodiments of the invention, this distance is held within 5 μm in all situations during ophthalmic surgery, which sets a margin of error for the procedure. It is possible that with future use and experimentation, it may be found that either more stringent or alternatively more lax displacement error tolerances are desirable to improve overall system performance.

Stabilization of a moving target requires defining the target, characterizing the motion of the target, and readjusting the aim of the apparatus of the present invention repeatedly in a closed-loop system. To meet accuracy goals also requires that the moving parts within the apparatus not contribute internal vibrations, overshoots, or other sources of positioning error which could cumulate to an error in excess of the prescribed dispositioning tolerances. There have been several previous attempts at achieving this result. Crane and Steel (*Applied Optics*, 24, pp. 527, 1985) and Crane (U.S. Pat. No. 4,443,075) described a dual Purkinje projection technique to compare the displacement of two different-order Purkinje projections over time, and a repositioning apparatus to adjust the isometric transformation corresponding to the motion. The tracking methods disclosed therein are based on a fundus illumination and monitoring device that aspires to distinguish translational from rotational eye movements, thus stabilizing an illuminating spot on the retina. However, localization of the Purkinje points can be influenced by transient relative motions between the various optical elements of the eye and may provide significantly fictitious position information for identifying the surface of the cornea. Motility studies as described by Katz et al. (*American Journal of Ophthamology*, 107: 356–360, "Slow Saccades in the Acquired Immunodeficiency Syndrome", April 1989) analyze the translations of an image on the retina from which the resulting coordinate transformation can be computed and galvanometric driven mirrors can be repositioned. In addition to the fictitious information discussed above due to relative motions between different layers of the eye, the galvanometer drives described by Katz usually are associated with considerable overshoot problems. Since saccades can be described as highly accelerated motions with constantly changing directions, overshoot errors can easily lead to unacceptable errors.

Bille et al. (U.S. Pat. No. 4,848,340) describes a method of following a mark on the epithelial surface of the cornea, supposedly in proximity of the targeted surface material. However, in one of the uses of the present invention, a mark made on the epithelial surface would change its absolute location due to changes in the structure and shape of the material, caused by use of the instrument itself rather than by eye motions. Therefore, a target tracking and laser positioning mechanism that relies on a mark on the surface of the cornea in order to perform corneal surgery such as described by Bille's tracking method would be expected to lead to misdirected positioning of laser lesions below the surface when combined with any suitable focused laser, as intended in one of the uses of the present invention. Moreover, one of the features of the present invention is to be able to perform surgery inside the cornea without having to incise the cornea. The main advantages of such a procedure are in avoiding exposure of the eye to infection and in minimizing patient discomfort. It would hence be counterproductive to mark the surface of the cornea for the purpose of following the motion of said mark. In another embodiment taught by Bille et al., the tracking is based on a reference provided by either on the eye's symmetry axis, or the eye's visual axis, with an empirically determined offset between the two. Tracking is then accomplished by monitoring the reflection form the apex of the cornea, thus avoiding the need to mark the eye, and/or rely solely on patient fixation. However, with this technique, as in the preferred embodiment taught by Bille et al., the tracking does not follow tissue features generally at the same location as the targeted surgical site on or inside the eye. Instead, Bille et al.'s techniques track reference points that are, in all cases, separate, remote from and may be unrelated to the targeted surgical site. Such methods compromise accuracy of tracking in direct proportion to the degree of their remoteness relative to the surgical site. Therefore, they do not adequately provide for the fact that the eye is a living tissue, moving and changing shape to some extent constantly. Tracking a single point on the cornea, when the cornea itself actually shifts considerably on the eye, thus cannot be expected to reflect positional change of the targeted surgical site.

By contrast, in the preferred embodiment of the present invention the tracking information is obtained through means contiguous to the target region, which is mechanically and structurally considered as part of the cornea, but is unlikely to be affected by the course of the surgery and can thus provide a significant representation of non-surgically induced displacements. This is a critical feature of the tracking method disclosed herein, in that involuntary motions of the eye (such as are caused by blood vessel pulsing) can now be accurately accommodated, unlike techniques that rely on remote reference points.

The accuracy of the apparatus and system of the invention preferably is within 5 $\mu$m, as determined by a closed-loop system which incorporates actual measurement of the target position within the loop. (For example, a microstepper motor based assembly may have a single step resolution of 0.1 $\mu$m verified against a motor encoder, but thermal gradients in the slides may yield greater variations. Moreover, position of the slide can be verified via an independent optical encoder, but the random vibrations of the target can invalidate the relative accuracy of the motor.) Thus, the surgeon has knowledge of the shape of tissues within the field of view and the precise location of where he is aiming the instrument within those structures, to an accuracy of 5 $\mu$m. Such precision was not attainable in a systematic, predictable manner with any of the prior instruments or practices used. The present invention thus seeks to obviate the need for binocular vision used to obtain stereoptic images in some prior methods (see., e.g., Crane, U.S. Pat. No. 4,443,075).

In a preferred embodiment of the invention, the instrument also ensures that a laser pulse is fired only upon command of the computerized controller and after the system has verified that the tracking assembly is still locked onto the desired location, that the energy being emitted by the laser falls within prescribed error tolerances, and that the aiming and focusing mechanisms have reach their requested settings. There is no need to separate aiming beam. In one embodiment of the present system, the method of parallax ranging is implemented to map out surfaces posterior to the cornea, but preceding actual treatment.

Safety is a very important consideration with laser surgery. In prior surgical systems and procedures, some safety shut-off procedures for laser firing have depended upon human reaction time, such as the use of a surgeon's foot pedal for disabling the instrument when a situation arises which would make firing unsafe. In ophthalmology, some instruments have relied as a safety feature on a pressure sensor located where the patient's forehead normally rests during surgery. If insufficient pressure were detected by the sensor, the instrument would be disabled from firing.

Such prior safety systems have inherently had slow reaction times, and have not been able to react quickly enough to all of the various problems which can arise during a firing sequence. This is a critical concern in ophthalmic surgery, especially where specific surgical procedures are to be performed near sensitive non-regenerative tissues, such as the corneal endothelium layer and the optic nerve. In contrast, the target capture and tracking system of the present invention makes available a new and highly dependable safety system. If for any reason, either prior to or during a given surgical procedure, the tracking system loses its target, the laser is disabled from firing. Various options are available for blocking emission from the apparatus once the tracking assembly has verified the loss of a tracking signal.

No previous surgical laser system has employed the efficacious combination of features as disclosed herein. For example, in previous art, Bille et al. (U.S. Pat. No. 4,848,340) and Crane (U.S. Pat. No. 4,443,075) taught tracking techniques to follow tissue movements which might occur during surgery, but did not teach simultaneous 3D imaging within the tissue to monitor the effects of surgery on the tissue and provide requisite safety margins; L'Esperance (U.S. Pat. No. 4,669,466 and 4,665,913) also did not suggest any aspects of 3D imaging, teaching only laser surgery on the anterior surface of the cornea; Bille (U.S. Pat. No. 4,579,430) shows a retina scanner, but does not teach simultaneous tracking. Bille et al. (U.S. Pat. No. 4,881,808) teach an imaging system and incorporate a tracker and a beam guidance system by reference (per U.S. Pat. Nos. 4,848,340 and 4,901,718, respectively) but fail to address the very difficult challenges involved in achieving a smooth combination of all these aspects into a single surgical laser unit with built-in high reliability features. By contrast, it is the unique integration of several such diverse aspects (including mapping, imaging, tracking, precision laser cutting and user interface), precisely yet inexpensively, into a fully automated workstation, the uses of which are transparent to the user, that is the main subject of the present invention. The methods and apparatus disclosed herein are thus expected to enhance the capabilities of a surgeon/user in accomplishing increasingly more precise surgical interventions in a faster and more predictable manner. Enhanced safety is expected to be a natural outcome of the methods and apparatus taught herein in that the surgery will be performed without many of the risks associated with competing methods and apparatus as described by L'Esperance (U.S. Pat. No. 4,669,466 and 4,665,913), Srinivasian (U.S. Pat. No. 4,784,135), Bille et al. (U.S. Pat. Nos. 4,848,340; 4,881,808; and 4,907,586), Frankhauser (U.S. Pat. No. 4,391,275), Aron-Rosa (U.S. Pat. No. 4,309,998), Crane (U.S. Pat. No. 4,443,075), and others.

SUMMARY OF THE INVENTION

An embodiment of the present invention is herein disclosed, comprising a method, apparatus, and system for precision laser based microsurgery or other laser-based micromachining, and including the following elements, each of which is described below.

(1) A final objective (lens), the axial position of which relative to the tear layer of the corneal vertex (or to a more general target), is held constant by an axial tracking means, and through which pass all optical radiations emitted or accepted by the system. (2) An axial tracking means (including associated optics) for maintaining constant separation between the final objective and its target (which is to be distinguished from the (common) target for the treatment means and the parallax ranging means, and also from the target for the viewing means) as that target moves axially along the final objective's centerline. The axial tracking means includes a compensation means to preclude it from being adversely affected by the transverse tracking means. (3) A transverse tracking means (including optics) for maintaining constant aiming between the treatment and parallax ranging means and their (common) target, and between the viewing means and its target, as those targets move (together) transversely to the final objective's centerline. (4) A treatment means for effecting the actual laser microsurgery/micromachining, including a laser, laser-beam directing optics, a treatment aiming means (with optics), and a treatment focusing means (also including optics), all of which are actuated by a computerized control means. (5) A parallax ranging means, which shares optics for the treatment aiming and focusing means, for positioning the common focus of the treatment parallax ranging means at a desired location (independent of the target identified above) by use of the viewing means and without requiring the actual operation to be performed. (6) A viewing means, comprising optics and a low-light-level TV camera, for presenting to the surgeon/user, on the display means, an adjustably magnified image of the volume adjacent to the viewing target, which target may be chosen by the user independently of the other targets identified above. (7) A computerized control means, including a user interface presented on the display means, which performs calculations and accepts and issues signals in order to execute the various functions of the overall system. (8) A display means for presenting to the surgeon/user he image from the viewing means plus computer-generated overlays from the user interface: such overlays include not only menus but also textual and graphic representations of aspects such as the topography of the cornea (or more general surfaces associated with the various targets) and the microsurgery/micromachining templates to be used. (9) A profiling means, including optics, one or more (patterned) profilometry illuminators, and a TV camera, to generate the data from which the computerized control means can calculate the topography of the cornea (or, in other embodiments, a more general surface). (10) An output measurement means to measure parameters of the laser radiation delivered to the eye of the patient or the workpiece. (11) Various illumination means, such as the profilometry illuminators, the coaxial illuminator, and the slit illuminator, to provide the light source(s) for the profilometry means, the transverse tracking means and the viewing means.

The present invention is expected to be useful in a variety of medical specialties, especially wherever the positioning accuracy of laser lesions is critical and where accurate containment of the spatial extent of a laser lesion is desirable. Much of the following discussions will be directed at ophthalmic applications and specifically corneal refractive surgery. This should not be viewed as a limitation on the applicability of the apparatus and method of the present invention. Alternate embodiments of the invention are expected to play a role in several other medical applications.

The system is also useful for non-medical operations, such as industrial operations, especially micromachining and short repair of microchips, wherein a focused laser beam is used to perform high precision operations on an object subject to movement, or in the automated inspection and correction of errors in the manufacture of microprocessors and high-density integrated circuits.

In specific applications to corneal procedures, the present invention is intended to provide a means by which an ophthalmologist can (a) observe the patient's eye at both low magnification to orient the procedure and at progressively higher magnification to provide great resolution for finer and more accurate procedures, (b) access on-line diagnostic information as to the shape of one or more relevant surfaces or of tissue layers to be treated, (c) describe a pattern of shots to effect a particular lesion shape without requiring manual aiming of each shot by the surgeon, (d) provide a therapeutic laser beam propagating through a beam steering and focusing delivery system which can localize the laser lesions at a particular depth in the immediate neighborhood of the laser focal point without appreciable damage elsewhere and with minimal peripheral necrosis or thermal damage surrounding the affected volume, and (e) provide a target tracking system that can minimize the error in positioning the pattern of the laser lesion in a moving target.

In the user interface, a video monitor screen is provided in front of the surgeon, and the screen provides a variety of choices for imaging and diagnostic information. Among the selections available to the ophthalmologist, for example, is a live video image of the eye superimposed over sectional perspectives of the shape of the corneal anterior surface and displayed along with the location where the proposed surgical lesion is situated. Another choice is to display a wire-mesh contour elevation map of said corneal surface together with an imbedded display of the proposed lesion. These selections can all be enlarged by using the zoom option which augments the live video image, and proportionally also the wire-mesh surface contour, the perspective views of the surface, and all other relevant diagnostics.

Additionally, a library of patterns is available so that the computer can generate templates based on the optical correction prescribed (generated off-line by the physician's "refraction" of the patient) and the measured topography (which templates will automatically correct for edge effects, based on built-in expert-system computational capability). The surgeon/user can move the templates on the screen by means of a trackball, mouse, or other standard pointing device for manipulating points on a video screen and thus, define the shape of the desired lesion and situate it at the optimal treatment location. These templates serve the additional function, once finally approved by the surgeon/user, of automatically controlling the path of the firing of the laser as well as the size and location of the laser-generated lesions to be formed in the course of the microsurgery. Since particular templates can be stored in computer memory, the surgeon/user may, as experience with the apparatus develops, draw on a bank of prior knowledge relating to a particular form of microsurgery, such as ophthalmic surgery directed to a specific type of correction. A physician may therefore choose to select from a set of pre-existing templates containing his preferred prescriptions, lay the template, in effect, on the computer-generated image of the region, and resize and/or re-scale the template to match the particular patient/eye characteristics. The surgery can then be executed automatically in a precisely controlled manner, based on the computer programming sense.

Such a pre-existing library of templates is also useful in the execution of controlled animal studies. It should be noted, however, that without the accompanying three-dimensional targeting capability and the automatic image stabilization means contained within the hardware of the present invention, the utility of template-generated surgery alone would be severely limited either to no-sensitive tissues (where high three dimensional precision is not usually a consideration) or to relatively stationary or immobilized targets (not usually available at high magnification in a biological system which is "alive").

In another embodiment of the methods and hardware of the present invention, templates can also be generated and stored in similar manner for procedures other than corneal refractive surgery, including iridotomy, posterior capsulotomy, trabeculoplasty, keratotomy, and the like.

Among the advantages of the present invention is the modular design of the multiple assemblies. The multiple assemblies are each individually supported on kinematic mounts. These mounts allow for the separate construction of the multiple assemblies, their alignment to tooling jigs individually, and the precise "hard-aligning" of the multiple assemblies into a complex optical system. Although such kinematic mounts can add, somewhat, to manufacturing costs, they save considerable alignment time during the assembly of the apparatus and provide a greater measure of reliability that the apparatus shall remain in operational alignment during continued use by non-technical surgeon/users.

Using the instruments of the present invention, the surgeon can generate a proposed pattern of therapeutic treatment, can compare the pattern to the actual tissues targeted, can compare his proposed surgery with what other surgeons have done in similar situations, and can still have the assurance that when he is finally satisfied with the proposed procedure, he can push a button to cause the desired surgery to be carried out at a high rate of independently targeted shots per second. This speed minimizes the risk during surgery at catastrophic patient motion.

In addition, the surgeon has at his disposal a fast reliable safety means, whereby the laser firing is interrupted automatically, should any conditions arise to warrant such interruption of the procedure. The surgeon can also temporarily disable the laser from firing at an point during the course of the surgery via suitable manual controls.

The tracking subsystem of the invention serves two important purposes: it tracks and follows the movements of the patient's tissue—not only the voluntary movements which can be damped with specialize treatment, but also the involuntary movements which are more difficult to control on a living specimen—and continuously re-presents an image of the same section of tissue. Thus, the surgeon/user is provided a continuous, substantially immobilized view of that tissue regardless of patient movements; and it further provides a fail-safe means for immediately stopping the action of the surgical laser beam in the even the tracking is lost, i.e., the tissue is not recognized by the tracking algorithm following the motion, per the discussion on safety features above.

In accordance with the invention, fast imaging and tracking are achieved using the combined effects of a pivoting tracking mirror which may be under the directional control of a piezoelectric or electromagnetic transducer, or other rapid servo device to pursue eye motions in a plane perpendicular to the optical axis of the final focusing lens (also referred to herein as the X-Y plane), coupled with a motor drive which translates the otherwise fixed final focusing lens assembly along the axial direction of the final focusing lens, herein denoted as the Z axis. Thus, three dimensional motions which fall within the domain of capture of the tracking system can be observed, pursued and captured.

Fast response times are possible with the described embodiment of the invention, limited by the ultimate speed of the tracking detector, the computational capabilities of the apparatus microprocessors and data transfer rates, and the moment of inertia of the tracking servo mirror. It has been determined that such closed-loop target recognition and tracking should occur at least at a rate of approximately 20-to-40 Hz in order to compensate for involuntary eye motion and thus, provide a significant improvement over human reaction times. Tracking rates on the order of 100 Hz for full amplitudes on the order of >1 mm (about 5°) in the transverse direction and in excess of 40 Hz over a range of +2 mm axially, would ultimately be achievable with some improvements based on the methods and system of the present system.

In a preferred embodiment of the present invention, the tracking sensors, or detectors, in combination with their circuitry, should be capable of high spatial resolution. Examples are linear position sensing detectors and quadrant detectors. For corneal refractive surgery, the limbus of the eye provides a landmark ideally suited for such detectors. In the retina, landmarks such as the optic disk, or vessel configurations can similarly provide landmarks upon which a magnified view can serve as the tracking landmark. In the present invention, any natural eye feature located in proximity of and structurally contiguous to the target site will serve as the tracking landmark. The important observation is that the location of the tracking landmark must respond to forces and pressures in a manner similar to the targeted tissues, yet it cannot be coincident with the precise target site itself, since this site will change during the course of the surgery.

Since the limbus is the outer edge of the cornea, it is expected that the limbus will respond to changes in position in a similar manner to other corneal tissues. The limbus further has the advantage of being contiguous to the sclera. Correspondingly, it is expected that the transient displacements occasioned by the impact of the laser pulse on the target site will be damped sufficiently at the limbus so as to not induce fictitious tracking signals. Such fictitious tracking signals would normally be a frequent observation if the present invention were to use, for example, a mark on the surface of the cornea in the vicinity of the operative site or a remote symmetry axis. Similar considerations apply when selecting a tracking landmark in other eye segments.

By incorporating intensified cameras, the present instrument and system is of high sensitivity, requiring only low levels of illumination, and produces video images of high contrast and high resolution. Illumination levels are kept well within established safety levels for the human eye. With the optics of the present system the patient's tissue is observed from an appreciable distance, sufficient for comfort to the patient even during surgery, and sufficient to permit the surgeon/user ready access to the patient in case of emergency, to insure safety at all times, to reassure the patient, or for any other reason which the surgeon/user may feel justifiable.

Zoom optics are included so that the physician an select a range of magnification for the video image, which maybe from about, say 15× to 200×. Different zooming ranges may be appropriate for different types of surgical procedures while maintaining an overall zooming capability of approximately 15-fold. The viewing system may be refocused in depth as well as transversely, independent of the treatment beam, as desired.

In one embodiment of the present invention, a system for use in ophthalmic laser surgery includes a laser source with sufficient output power to effect a desired type of surgery in the ocular tissue, along with an optical path means for delivering the laser beam, including beam directing and focusing means for controlling the aim and depth of focus of the laser beam. In a preferred embodiment of the present invention, a laser firing up to 250 shots per second is employed. Such a laser device can generate an intricate pattern consisting of 50,000 shots aimed separately at different locations in under 4 minutes. For most types of ophthalmic surgery procedures falling in the domain of application for the system disclosed herein, the method of deposition of the laser pulse energy onto the target site calls for achieving irradiances at the target site above the threshold for ionization of molecules within the target site and giving rise to an avalanche process culminating in plasma formation. Since the maximal diameter of the lesion will consequently not be determined by the theoretical spot size of the laser beam but by the maximal outward expansion of the cavitation induced during plasma collapse, and since the maximal lesion capacity of the plasma is related to the amount of energy transferred into the plasma volume (and subsequently into a shock wave) by the laser pulse, considerable attention is needed to maintain the laser pulse energy within narrow variation tolerances. In one preferred embodiment of the present invention, this is achieved by a closed feedback loop, wherein each laser pulse emitted by the system is sampled to determine the actual energy being emitted. Any trends in emission energy can thus be identified allowing subsequent emitted pulse energies to be adjusted accordingly.

U.S. Food and Drug Agency regulations for medical laser devices currently require manufacturers of said devices to provide a means for measuring the output delivered to the human body to within an accuracy of +/−20%. There is no specification on emission tolerances for the laser beyond the constraints of safety and efficacy. However, verification of average pulse emission does not preclude 50% variations between consecutive pulses in a firing sequence. Such variation range is one of the reasons why "misfires" occur in many ophthalmic devices. It is not that the laser failed to fire, but that insufficient energy was emitted to achieve the desired or expected result because of unforeseen and undetected energy variations. For an automated system, such as the present invention, the emission for the laser needs to be monitored and adjusted to achieve far narrower pulse-to-pulse error tolerances.

In summary, it is among the objects of the present invention to greatly improve the accuracy, speed, range, reliability, versatility, safety, and efficacy of laser surgery, particularly ophthalmic surgery, by a system and instrument which continuously presents information to the surgeon/user during surgery as to the precise location, aim, and depth of the surgical laser and also as to surrounding features of the subject tissue, in three-dimensions. It is also an object of the invention to track movements of the subject tissue during surgery, particularly critical in eye surgery where eye movements can be very rapid and involuntary. It is further an object of the invention to provide a safe means of first establishing a reproducible firing sequence positioned in a three-dimensional space, and then firing the sequence in high repetition rates, thus obviating the time-consuming need to repetitively inspect, aim, and fire each shot before proceeding to the next target. Still another object is to provide a system applicable to non-medical fields wherein a laser beam is used to effect a precise operation on a target or series of targets subject to movement during the procedure. These and other objects, advantages, and features of the invention will be apparent from the following description of preferred embodiments, considered along with the accompanying drawings.

It is an object of the present invention to accommodate much more demanding tolerances in laser surgery, particularly eye surgery but also for other medical specialties, through a method, apparatus and system for high-precision laser surgery which provides the surgeon "live" images essentially in real time, containing the full supporting diagnostic information about depth and position at which a surgical laser will be fired. In a computer, the full information content of a given signal is interpreted so as to provide this supporting diagnostic information, and the resulting accuracy achievable is within a few human cells or better.

BRIEF DESCRIPTION OF THE DRAWINGS

In FIG. 1 the workstation is configured for ophthalmic surgery.

DESCRIPTION OF THE SPECIFIC EMBODIMENTS

Figure 1:
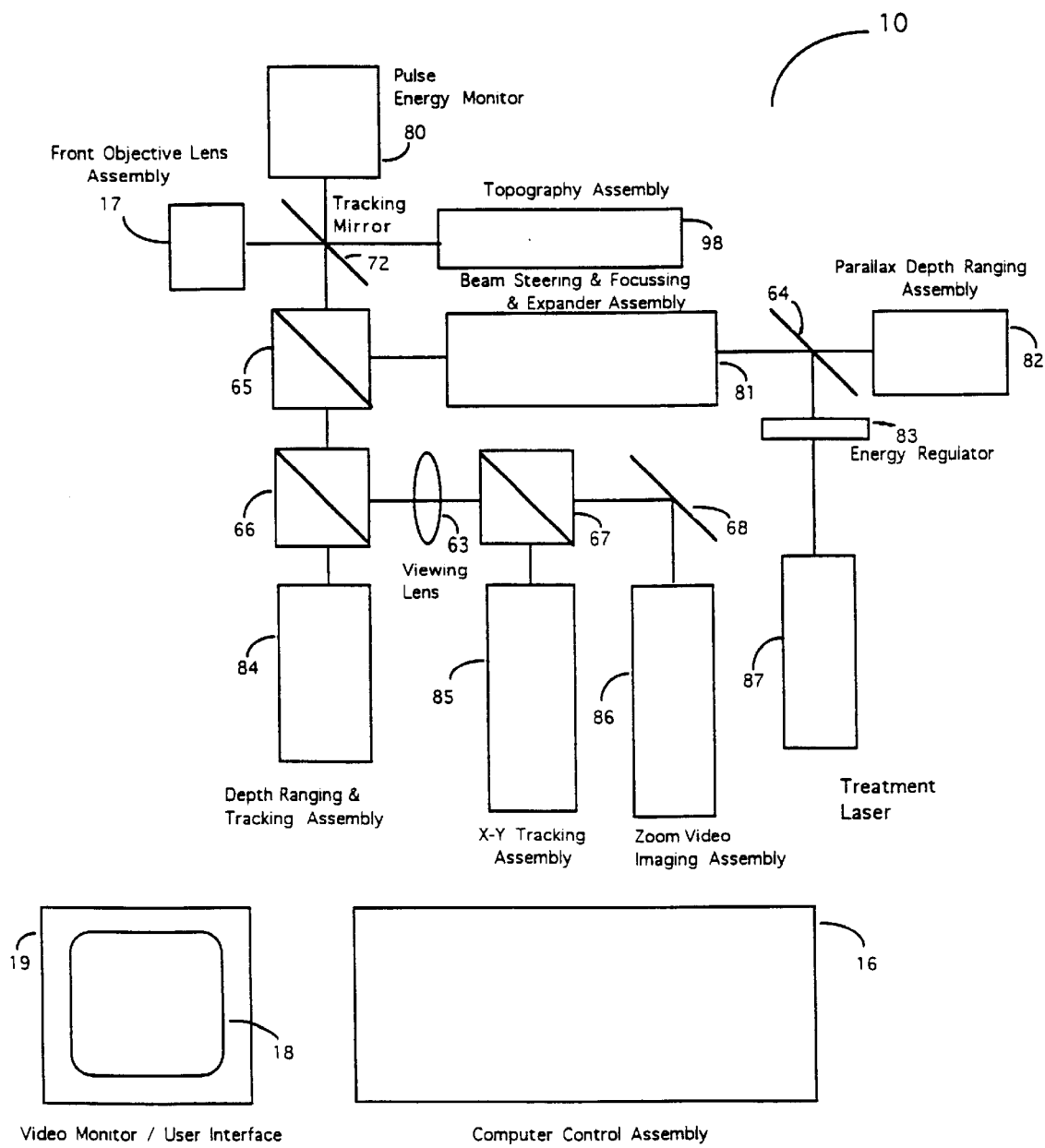
FIG. 1 is a block diagram of an instrument or workstation for performing precision laser surgery in accordance with the principles of the present invention.

In the drawings, FIG. 1 shows a block diagram for the fundamental assemblies of a complete precision laser surgery and/or diagnostic/analytical instrument 10 in accordance with the principles of the present invention, in the form of a workstation. Not shown are the support station housing the video monitor means, the power supplies, the fire control/safety switch, and other accessories for the workstation.

Although the system, apparatus, and method of the invention are illustrated and discussed with reference to ophthalmic surgery and diagnosis, it should be understood that the invention encompasses other types of medical diagnostic and surgical procedures, as well as non-medical operations (e.g., semiconductor wafer processing, such as precision wafer fabrication, short repair using lasers and other micromachining techniques.)

The instrument and system 10 of the invention include controls 16 for a vision system and laser firing, enabling the surgeon/user to survey the topography and internal features of the tissue to be operated upon (the eye in the illustrated workstation) via a video means 19, and, via the computerized control means, to precisely control the timing as well as the direction, depth and spatial pattern of firing of a laser beam in three-dimensions. As will be explained below, the surgeon may control the firing of the laser with "templates" which can be superimposed over an image of the tissue being operated upon, and which enable an automatic tracing of desired laser firing pattern based upon prior experience or a surgeon's insights with similar surgical procedures. The templates may be pre-programmed or generated anew for each patient, as the case requires.

The system also includes a final objective lens or focusing lens or front lens 17 (an element of the microscope assembly, as explained below), through which images are taken and through which the laser beam is directed at the subject tissue. In a preferred embodiment of the system, an axial illuminating light beam may be projected at the tissue through the topography assembly 98 and the final objective lens 17. In other embodiments of the present invention, an off-axis slit illuminator, providing a ribbon-shaped illuminating light beam, may be used to augment and/or replace the axial illumination technique, (See Howland et al. "Non-invasive Assessment of the Visual System Topical Meeting," Santa Fe, Feb. 4–7, 1991) depending on the particular kind of surgical procedure or error tolerances required thereof. Th instrument 10 may contain, in addition, the therapeutic laser 87, the surgical microscope 86, an X-Y tracking assembly 85, a depth ranging microscope 84, a parallax depth ranging assembly 82, various illuminators, and the beam steering and focusing assembly 81. All of these assemblies share an optical path defined by the final tracking mirror 72 and the lens 17.

Tracking mirror 72 represents a key element in the system, in that it is in the path of light (whether transmitted or reflected), generated and/or acquired by all the various subassemblies of the workstation, excepting only the slit illuminator (of the alternate embodiment, not shown in FIG. 1). In alternate embodiments of the invention, the tracking mirror may be driven either piezoelectrically or electromagnetically. A piezoelectric driver uses the change in shape of a quartz crystal in response to an electric current to move the mirror. An electromagnetic driver uses a coil of wire in a magnetic field which is made to move by passing an electric current through the coil. The electromagnetic driver is similar in function to a voice coil of an audio speaker. In either embodiment, the speed (or, more accurately, the acceleration) of the entire tracking system is limited by the response of the drivers and the mirror's moment of inertia.

Most of the major components and subassemblies, shown in the block diagram of FIG. 1, are disclosed separately and have been incorporated herein by reference. However, the combination of these separate inventions into system 10, the methods by which they can be made to work in concert as an integrated unit, and the enhanced capabilities this entails in a surgical environment are the subject of the present invention.

For example, the topography technique requires establishing precisely the distance from the surface to be measured to the appropriate principal lane of the front focusing lens. Whereas there are several methods for establishing said distance, the modified confocal technique described by Fountain (U.S. Pat. No. 5,283,598) represents a preferred embodiment of such a measuring technique, incorporated by reference into the present invention. Since in surgery the targets are live tissue and are continuously in motion, to achieve high levels of accuracy requires that the surface to be measured by way of the topography assembly also remain stable with respect to the measuring sensors located within topography assembly 98, zoom video assembly 86, and the known focal point of laser 87. This is achieved by continuously adjusting the position of final focusing lens 17 along the axial direction as further described by Fountain in the '598 patent.

Figure 2:
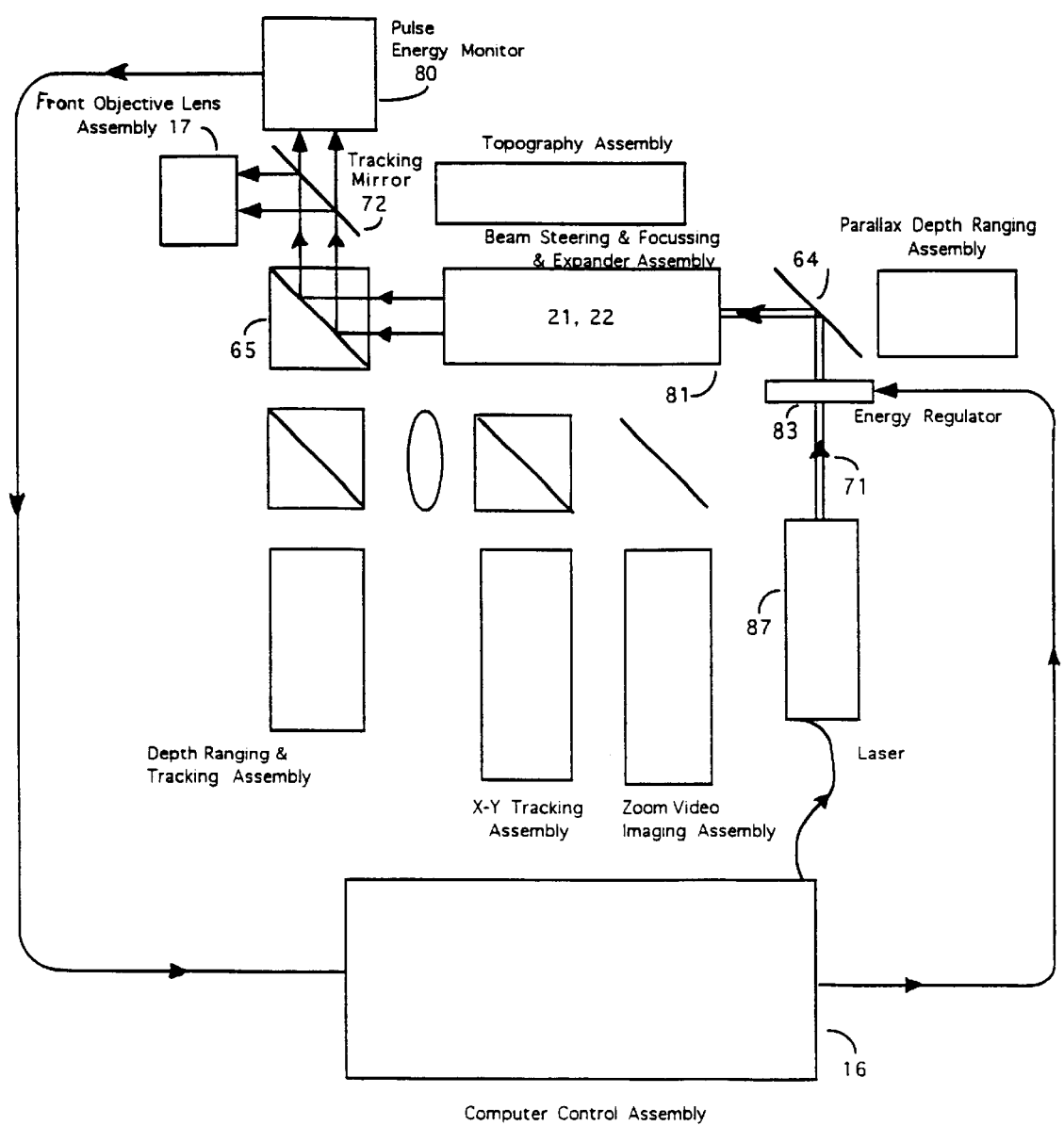
FIG. 2 is a block diagram of an instrument or workstation indicating the path of the laser energy pulse as it propagates through the system along with the functions of control and information flow among various optical components, detectors, and controllers for monitoring the energy of the laser pulse and maintaining the emission within prescribed narrow error tolerances.

FIG. 2 shows the light path 71 as it emerges from laser 87, passes through the external energy regulator 83, is expanded and directed in the beam steering and focusing assembly 81 as further described by Fountain et al. in U.S. Pat. No. 5,391,165 and is aimed via tracking mirror 72 and through front focusing lens 17 onto the prescribed target site. In a preferred embodiment of the invention, tracking mirror 72 will have an optical coating which will permit a small portion of the laser energy to continue through tracking mirror 72, along path 73 to be detected in energy monitoring assembly 80, as depicted in FIG. 2.

The pulse energy sensed in energy monitoring assembly 80 is electronically relayed to the computer control assembly 16 which in turn analyzes the output energy from laser 87 and adjusts the proportion of laser energy of subsequent laser pulses to pass through energy regulator 83. In an embodiment of the present invention, energy regulator 83 is a polarizer adjusted to be "crossed" with the polarized laser pulse, preceded by a rotatable half-wave retardation plate. Energy monitor 80 consists of an integrating sphere and detector which can record energy on a pulse-by-pulse basis. The energy detector calculates weighted exponential moving averages, modified with a weighting factor, as well as the rate of change of the running average. The accuracy of measurement of the pulse energy is within 5%, based on calibration against standard energy meters (e.g., Molectron, Scientech).

In a preferred embodiment of system 10, the steering, focusing, and aiming subassembly 81 may consist of a beam expander 22 that provides depth of focus variations through change of collimation, and a dual set of Risley prisms (also known as Herschel prisms) 21 to steer and aim the beam, as described in detail in the '165 patent by Fountain et al. (previously made of record).

Beam expander 22 may comprise a set of lenses 23, a stepper motor 41, and a slide 43 with 75 mm traverse corresponding to ~25 mm in the eye. Beam focus accuracy to within 10 $\mu$m can be provided in this manner, based on standard optical components. The Risley prisms are selected as preferred means of beam steering and directing because of lower moment of inertia and shorter lever arm as compared to alternatives, such as gimbaled mirrors. The lower moment of inertia inherently allows faster aiming (which is enhanced by the use of cylindrical coordinates, these being more natural for the eye than Cartesian coordinates), while the shorter lever arm permits aiming further off-axis without beam-clipping (vignetting) at the aperture of objective lens 17.

In a preferred embodiment of the invention, surgical laser 17 emits radiation in the visible wavelength range to take advantage of the transmission properties of visible light in the optically clear tissues of the human eye. One preferred embodiment of the invention uses a frequency doubled Nd:YAG laser, producing sufficiently short duration pulses (shorter than a few hundred nanoseconds, and preferably shorter than 10 nanoseconds) to limit the amount of energy required to ionize material as discussed further below.

In alternative embodiments, laser 87 may be one of several types of flashlamp- or diode-pumped solid-state lasers (such as, Nd:YAG, Nd:YLF, HoYLF, Er:YAG, alexandrite, Ti:sapphire or others) operating in the fundamental or a frequency-multiplied mode, a semiconductor laser, or an argon, excimer, nitrogen, dye, or any of a host of different laser, or combinations thereof, currently available or in development. The present invention can be used with any of a wide variety of lasers by specifying different coatings where necessary for the optical surfaces. A quartz and magnesium fluoride focusing element is available as the element 17 to accommodate ultraviolet lasers whether they be excimer lasers or frequency shifted solid-state lasers. One of the features of the present invention is that is it is not laser specific, but represents a surgical instrument intended to enhance the efficacy of any therapeutic laser. Laser 87 preferably produces a pulsed beam which is controllable as to the level of energy per pulse, pulse peak power, and repetition rate. For ophthalmic applications which do not seek to generate laser lesions below the front surface of the cornea, or wherever incising the eye is an acceptable option as a preliminary or as part of the procedure, then excimer lasers, holmium lasers, carbon dioxide lasers, or some other ultraviolet or infrared laser may be an acceptable modality. In one embodiment of the present invention, the surgeon is not restricted to surface effects or to incising the eye. With the same visible wavelength laser (for example, a frequency doubled Nd:YAG) the surgeon can select any tissue depth (whether on the corneal surface or below, whether on the posterior lens capsule or in the lens nucleus) at which to generate an effect without the necessity of exchanging laser modalities for different eye segments, provided there remains an optically clear path to the targeted layer in the corresponding visible range.

In the event of a non-visible-wavelength laser beam is used (e.g., strictly for ablating the front surface of the cornea, or strictly for coagulating blood vessels in the retina, or strictly for photodisrupting membranes on the posterior capsule) some variations in the optical configuration of system 10 will likely be required.

Figure 3:
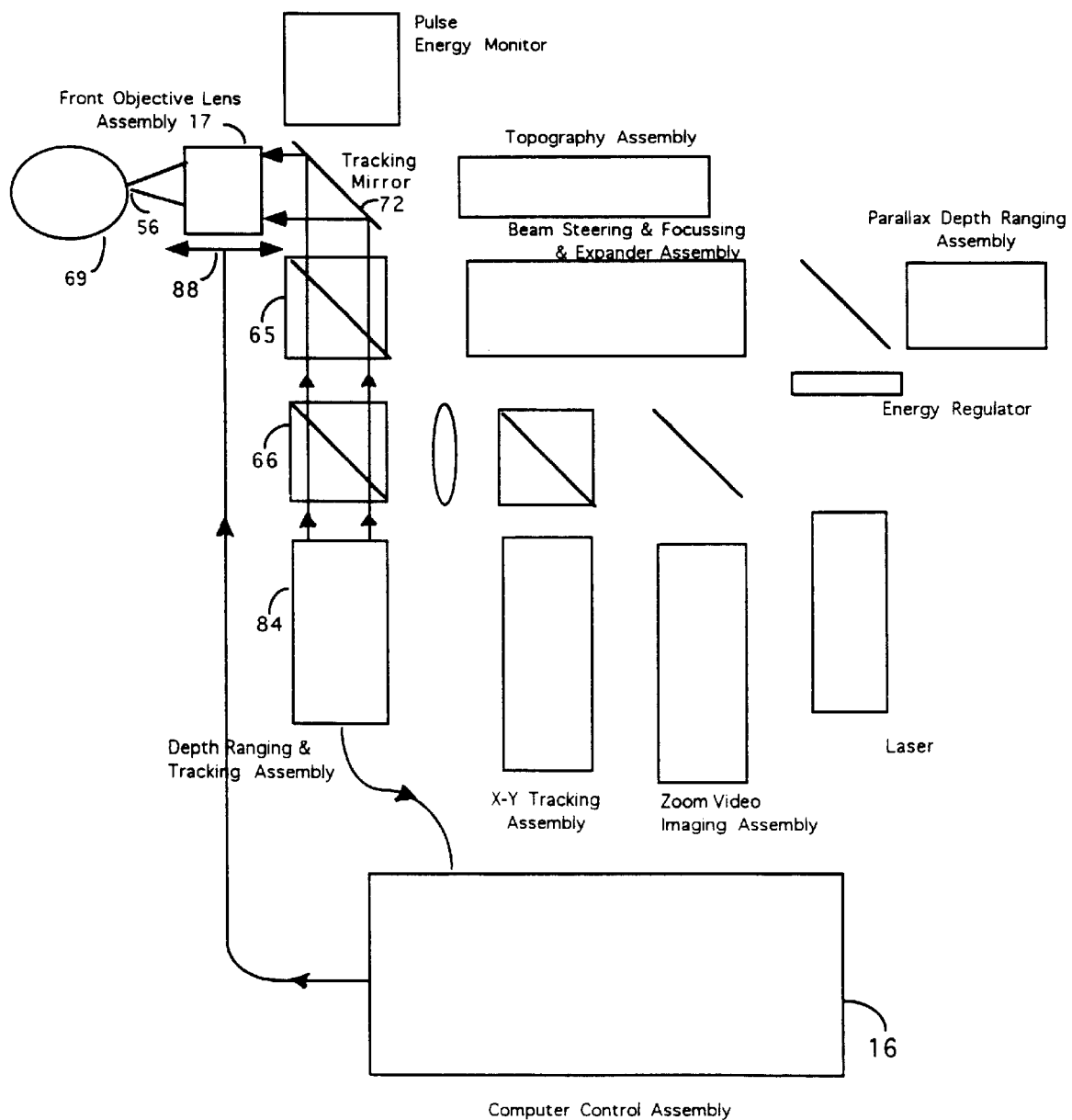
FIG. 3 is a block diagram of the path for light traveling from and back to the depth ranging or Z-plane tracking means, together with the loop for information flow to the computer control means and back to the position means.

FIG. 3 shows the information path for depth ranger assembly 84 that measures the distance from front focusing lens 17 to the surface of the eye 69 and continuously adjusts the position of front focusing lens 17 along path 88. In a preferred embodiment of the present invention, the path length 88 over which front focusing lens 17 is adjusted is 5 mm. The system comprising subassembly 84 together with lens 17 and the intervening optics, is sometimes referred to herein as the confocal microscope. It uses optical elements in common with other equipment of system 10, namely the tracking servo mirror 72 and beam splitters 65, 66. Focusing lens 17 is adjusted as to focus, along a Z-axis, in response to shifts in the depth of the subject tissue feature, so that the system always returns to a focus on the corneal vertex 56 (the part of the cornea that is closest to the objective lens).

Included in the depth ranger assembly 84 are depth tracking or "Z-axis" tracking sensors 50 which detect a change in location of the surface 69 as described by Fountain (in a U.S. Pat. No. 5,283,598, previously incorporated) and relay the information to the computer control assembly 16 which computes a new desired position for front objective lens assembly 17 and issues instruction to a motor drive to relocate said lens assembly 17 to the desired new location. A closed-loop is thus described which incorporates the live movements of eye surface 69 within the decision process of adjusting the focal point of lens assembly 17, to within given tolerances. In this embodiment, the capture range for axial acquisition is within +/−0.2 mm and tracking rates in excess of 40 Hz are within the servo loop capability for maximum ranges on the order of 2 mm.

Since mirrors and beam 64, 68, and 72, together with beam splitting cubes 65, 66 and 67, link the other assemblies of system 10 into a common axial path passing through lens focusing assembly 17, they can all be referred to the lens assembly 17 as if the distance between lens 17 and eye surface 69 were to remain constant. This is a major simplification in the manner in which eye surgery can be performed in that the surgeon need no longer be continuously monitoring eye movement to verify a constantly changing focal position within the patient's eye.

Figure 4:
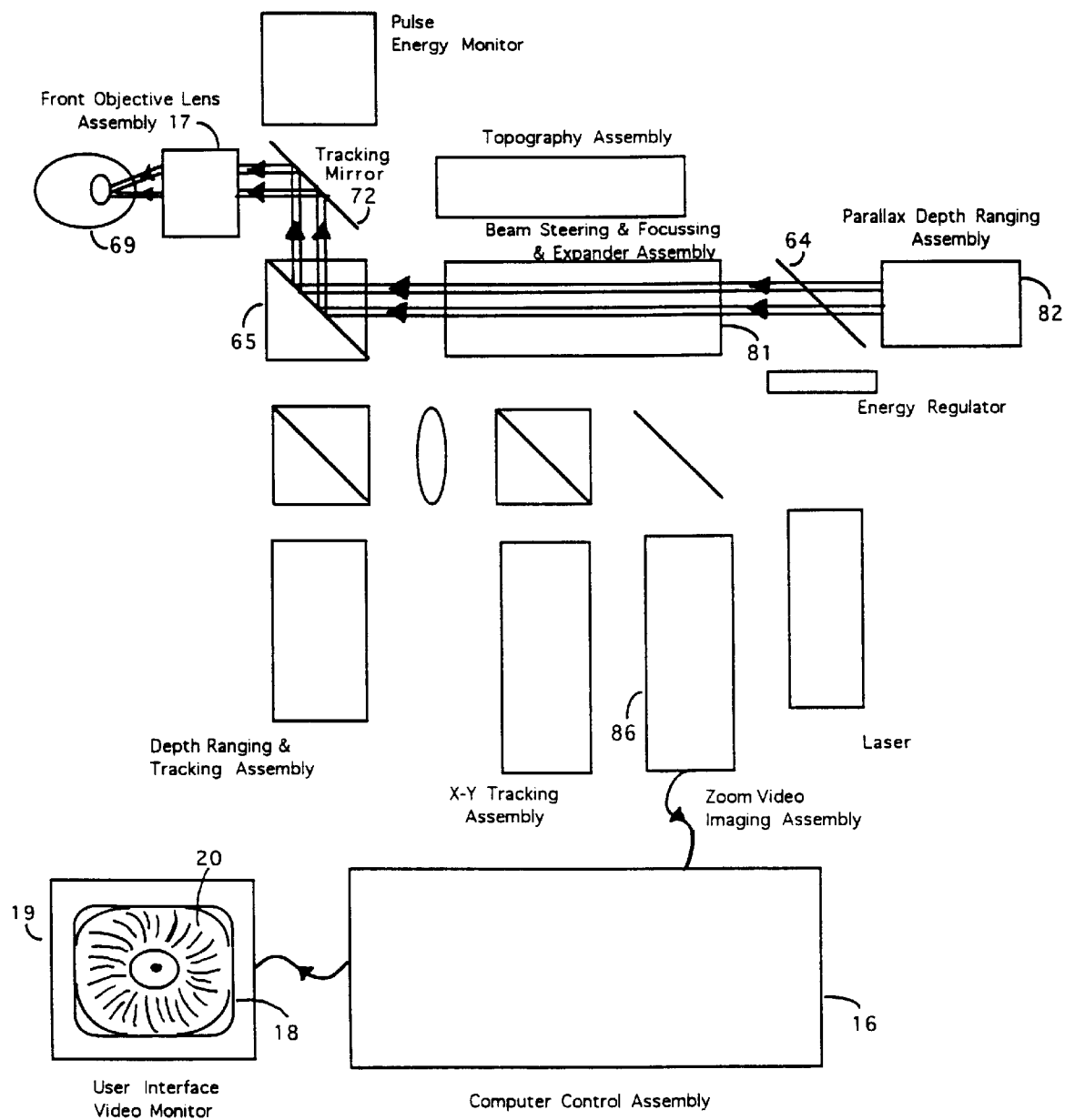
FIG. 4 is a block diagram showing the light path from the parallax ranging assembly to the eye and the control path from the imaging video camera to the video monitoring display means. The light path from the eye back to the imaging camera is also indicated in this Figure.

For procedures where the targeted tissue layers lie posterior to the cornea, the surgeon/user will have the use of the parallax depth ranging instrument 88, as shown in FIG. 4. This assembly relies on the intersection of two beams of light (from, e.g., a He—Ne illuminator laser) converging to a common point on a given surface. In one embodiment, the parallax ranger allows mapping of a mesh of points, acquired through judicious adjustment of the zoom camera to short depth-of-focus (maximum magnification), which, along with corresponding variation of the focus on the parallax ranger, produces a series of diffraction limited spots on the structures behind the cornea (iris, lens, etc.). In this manner, the resulting surface will define a desired template.

The inclusion of a parallax ranger within instrument 10 overcomes difficulties commonly associated with specular reflection techniques used for detection of the location and measurement of ocular features. Basically, only the tear surface layer overlying the corneal surface epithelium is usually detectable and measurable by specular light reflection techniques. The reflected light signal is generally insufficient for the extraction of topographic information of the endothelium surface of the cornea (<0.02% reflection versus 4% from the epithelium), let alone for characterization of the three-dimensional shape of the anterior and posterior capsules of the crystalline lens of the human eye. The parallax ranger unit provides the surgeon/user with the option of using a combination of standard techniques which rely on images of a target site. Thus, the surgeon/user can identify, to within the inherent error tolerances of the technique, when the instrument is focused on a given surface. The precise focal point of the beam can then be varied by altering the incoming beam divergence by way of defocusing a beam expander means 22 (included within assembly 81). By redefining the origin of a given procedure to coincide with the depth at which the parallax ranger is focused on a surface, this new identified surface becomes the reference surface for performing a surgical procedure. Via the user interface (See Sklar et al., U.S. Pat. No. 5,098,426 and U.S. patent application Ser. No. 475,657 (now abandoned), previously incorporated by reference), the surgeon/user can then define lesion templates or configurations to be performed at a given depth with respect to the new identified surface.

Similarly, the motion of the eye along a plane perpendicular to the Z-axis of front focusing lens assembly 17 also needs to be stabilized. This is achieved using the X-Y tracking path shown in FIG. 5. Intrinsic to any tracking scheme is the choice of what is to be tracked. If the eye were a non-deformable body, then any landmark on or in the eye would suffice for defining the motion of said material. However, the eye neither moves nor deforms as a rigid body. Consequently, in order to define the location of a moving tissue layer within the eye, the tracking landmark must be located contiguous to the targeted tissue and should mechanically respond in a manner similar to the targeted issue.

For corneal refractive surgery, the eye limbus at the radially outward edge of the cornea satisfies these constraints. It has the advantage of not only moving with the cornea—inasmuch as it is a part of the cornea—but, since it likewise is connected to the sclera, it will not respond as dramatically to the transient deformations associated with the microsurgery. In effect, pursuing the motions of the limbus will allow the computerized control system to replicate the template pattern presented on the display by the user interface, even though the eye surface will be appreciably deforming during the course of the surgical procedure.

In one embodiment of the invention, the transverse X-Y tracking detector consists of high speed quadrant detectors and a microprocessor such that updated position information is fed to the tracking mirror at frequencies substantially higher than the repetition rate of the laser, or the frame rate of the imaging camera. The response time of the tracking detector and processor should be sufficiently faster than the maximum repetition rate of the laser, so that laser firing can be disabled, if necessary. The response time of the detector and processor should also be higher than that of the driven tracking mirror, which must be capable of sufficiently high acceleration and velocity to compensate for the fastest motion possible by the intended target.

Figure 5:
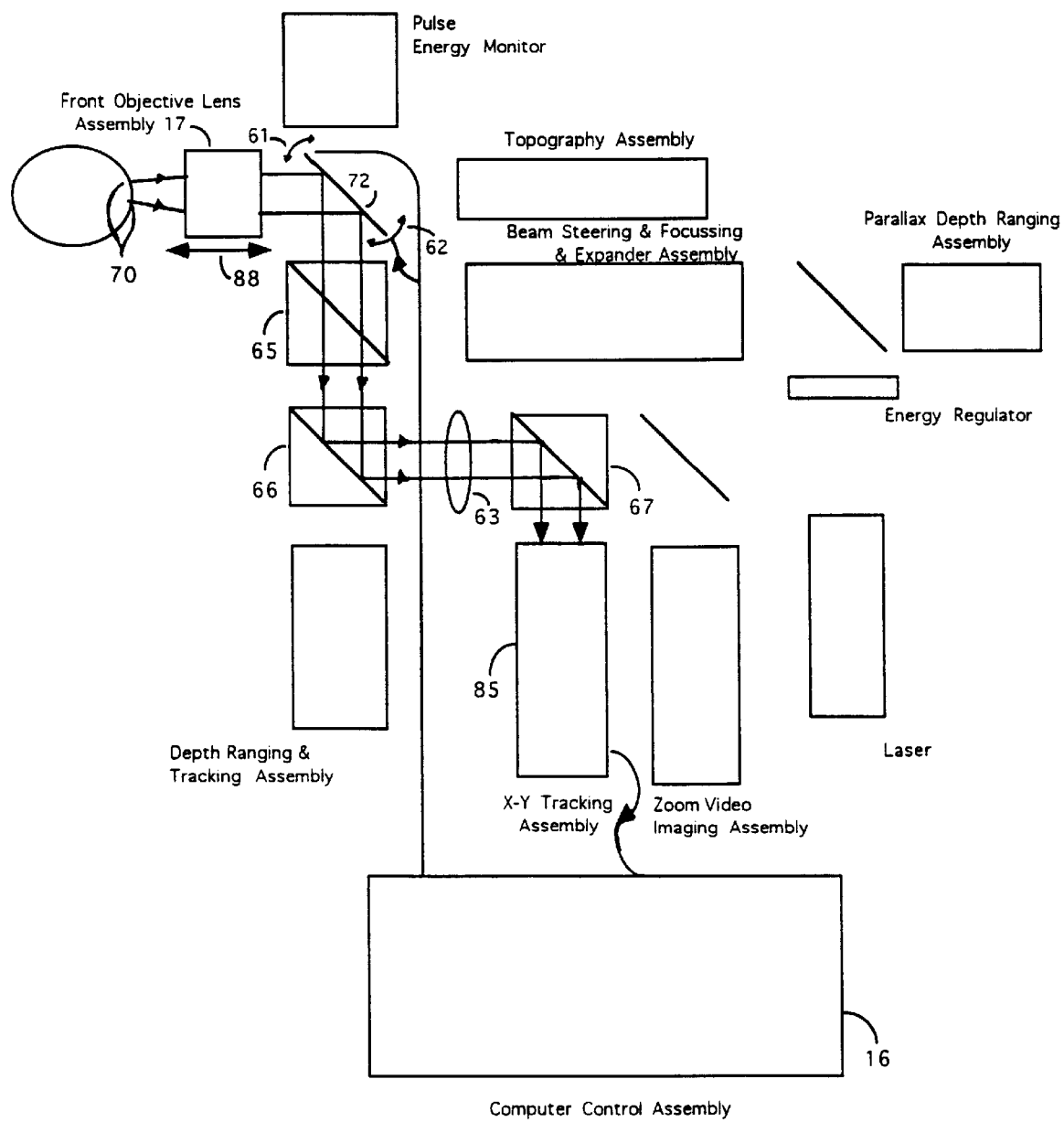
FIG. 5 is a block diagram of the workstation in which the light paths and control loops for the X-Y place tracking means are shown.
Figure 5A:
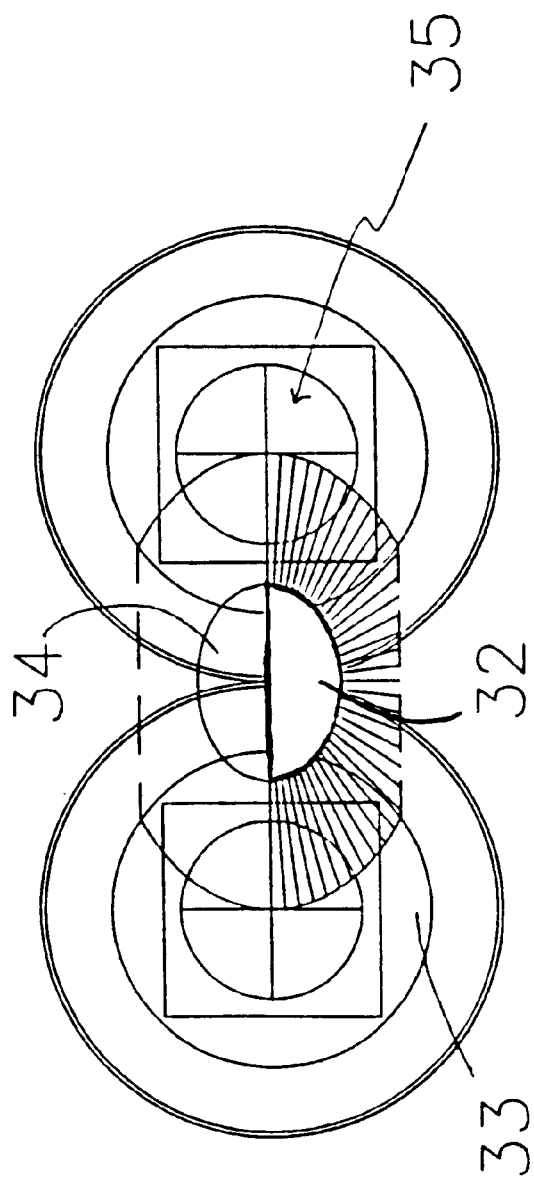
FIG. 5A shows the image of the iris incident on the two quadrant detectors used in a preferred embodiment of the sensor for X-Y tracking.

In FIG. 5, light from limbus 70 passes through the objective lens assembly 17, is reflected by the X-Y tracking mirror assembly 72, and is propagated via beam splitting cubes 65, 66 through viewing lens 63 to be reflected off beam splitter 67 to sensors of X-Y tracking assembly 85. In one preferred embodiment of the present invention, a spatially sensitive sensor 50 comprising two quadrant detectors is used to track an image of the outer rim (at the limbus) of the iris 32. As shown in FIG. 5A, the image of quadrant detectors (each with four quadrants 35, in this example) will then consist of a bright lune-shaped field corresponding to sclera 33, adjacent to a darker field representing an image of the iris 32. The very dark central core which is an image of pupil 34, is not captured by the detectors, as FIG. 5A illustrates, leaving a single sharp boundary to track. With various cells of the quadrant detector connected through differential amplifiers and normalized by the sum, the resultant signals are sensitive only to the position of the centroid of illumination of any of the above patterns. Quadrant detectors integrate the image illumination striking each quarter of the detector face. The luminosity impingent on the detector faces will then generate voltage differences corresponding to the integrated differences in light hitting the detector parts. A change in background light intensity will be ignored, as the increase across the four (or eight) quadrants 35 of the detector face will remain the same. Voltage sums and differences among the quadrants serve to establish the relative direction of motion between two contiguous readings of the limbus position. A shift in intensity at the sensor is thereby traced to motion of the limbus. These dedicated quadrant detectors record voltage changes extremely rapidly and can observe and quantify contrast changes and edge motions in less than 100 ms. In alternate embodiments, similarly fast but more sensitive position sensing detectors are used in this application, yielding enhanced performance at even lower light levels.

The voltage change information is relayed to the computer control assembly 16 wherein the actual coordinate shift is calculated. Control assembly 16 then determines the angular corrections to be relayed to the X-Y tracking mirror assembly 72 and activates a voice coil or other electromagnetic drive assembly to pivot the orientation of mirror 72 so as to stabilize the X-Y motion of limbus 70 with respect to system 10. This embodiment of a tracking system uses entirely analog signals and techniques to achieve tracking and can be made to work significantly more rapidly than even the fastest involuntary motions of the eye.

In one preferred embodiment of the invention, the range of use, or travel, is 2 mm in the X-Y plane. For ophthalmic applications, where the principal motions of the eye are rotations, it is often preferable to define the range of use in terms of angular sweep of the eye. For example, an angular motion of the eye of 5° falls well within the domain of use of the X-Y tracking system. For a sighted human patient, it has been estimated that such range of use will acquire an eye looking at an image point located in the far field (relative to the patient) and situated along the optical axis of the apparatus.

The transducers of the tracking system adjust the position of the X-Y mirror along two rotational axes at accelerations on the target in excess of 20 µm/ms for full amplitudes of over 2 mm, based on microprocessor-provided information relating to the new location of the same tissue.

Eye surface 69 may be displaced in translation and/or by rotational motions centered on the globe of the eye; because the X-Y tracking mirror 72 rotates about a point within its assembly that is different from the eye's center of rotation, a desired change in X-Y tracking mirror position also requires a correction of the X-Y axis position of the depth ranging and tracking assembly 84. Consequently, the algorithm which pivots the X-Y tracking mirror 72 along paths 61 and 62, also must relay instructions to the computerized control system to adjust the depth tracking and ranging assembly 84 so as to maintain the correct orientation. The preferred methods to achieve this correction use a compensating mirror 60 within the Z-tracking assembly (not shown in FIG. 5).

The tracking system has the advantage of being able to find an absolute position of the target even after a temporary loss of tracking. For example, if a surgical procedure is in process and an obstacle, such as a blinking eyelid in many ophthalmic procedures, interposes the tracking image such that the procedure is interrupted or temporarily aborted, the tracking system will automatically store in memory the last position in the firing sequence so that once the target is again reacquired, the exact location of the next point in the firing sequence can be determined automatically and the servo mirror be repositioned accordingly.

Figure 6:
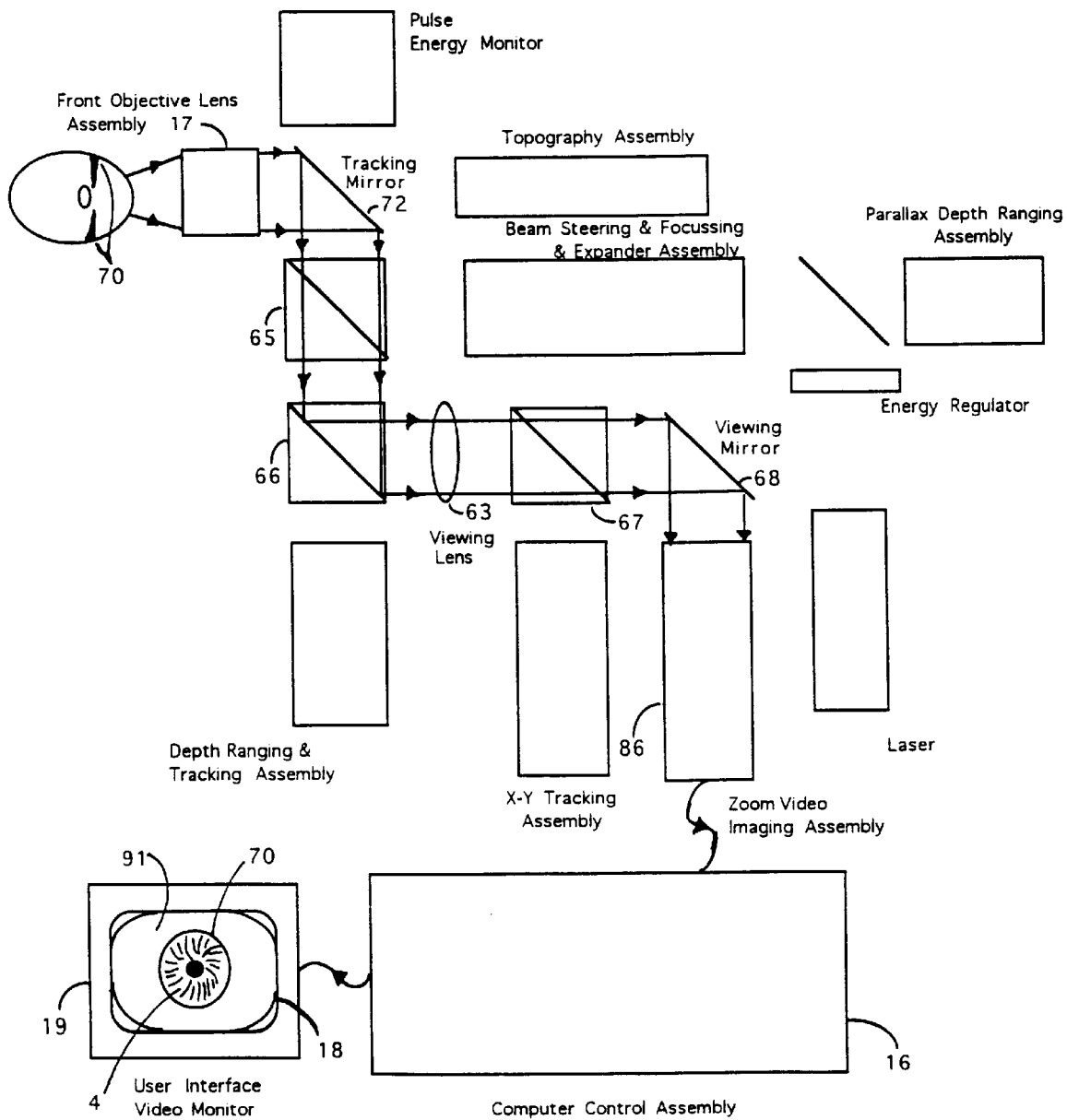
FIG. 6 is a block diagram indicating the interplay of the imaging means with the video monitor display.

FIG. 6 shows the surgical microscope loop. This subassembly includes the low-level-light camera and the zoom optics. The camera preferably comprises an intensified video camera, for example a silicon intensified target (SIT) tube camera. Alternatively, it can be a conventional video camera in combination with a microchannel-plate intensifier. In either event the camera's sensitivity preferably is about 1000 times that of a normal video camera, enabling the system to look at weakly scattered light and targets poorly illuminated for the desired levels of high magnification at large working distances.

In a preferred embodiment of the present invention, the system uses a combination of specular and scattered light techniques for detecting and identifying diffusely reflecting surfaces, specularly reflecting surfaces, surface displacements, features, and shapes of the patient's tissue. This is particularly useful in the eye where it can prove difficult to differentiate between the amorphous tear layer anterior to the cornea and the structured epithelial surface layer of the cornea. Even the cell walls of the endothelial cells of the cornea or of the anterior lens capsule will scatter light. The intensified surgical microscope can produce an image of these actual cells by forming an image composed by detecting scattered light. The surgical microscope, as well as the tracking camera, can substantially exclude specularly reflected light by cross polarization of selectively polarized illuminators. Other methods for reducing specular reflections preferentially to scattered images are also possible.

The microscope optics are designed to provide flat field, anastigmatic, achromatic, nearly diffraction limited imaging with optical magnification zoomable approximately over a 15-fold range of, say 15×–200×. The magnification is adjustable and is typically selected to correspond to the largest magnification which can still be comfortably used for situating a lesion (that is, the smallest field of view which can be used when magnified across the fixed display size of the video monitor.) For example, for corneal refractive surgery, where the surgeon needs to observe the cornea from limbus to limbus, this corresponds to a field of view of approximately 12 to 14 mm. At the screen, the zoom optics allow for adjustable magnification in the range of about 15×–200×, for example. This enables the surgeon to view a very narrow field, on the order of a millimeter in width, or a much wider field at lesser magnification. This is useful in enabling the surgeon to assure himself that he is aimed and focused at a particular desired region. Zooming can be effective through use of ajoystick, trackball, mouse, or other pointing device 42 to access a scroll bar in the user interface.

The function of the viewing mirror 68 shown in FIG. 6 is to move the surgical microscope image on the screen to the left or right or up or down, independent of the aiming of any other subsystem.

Figure 7:
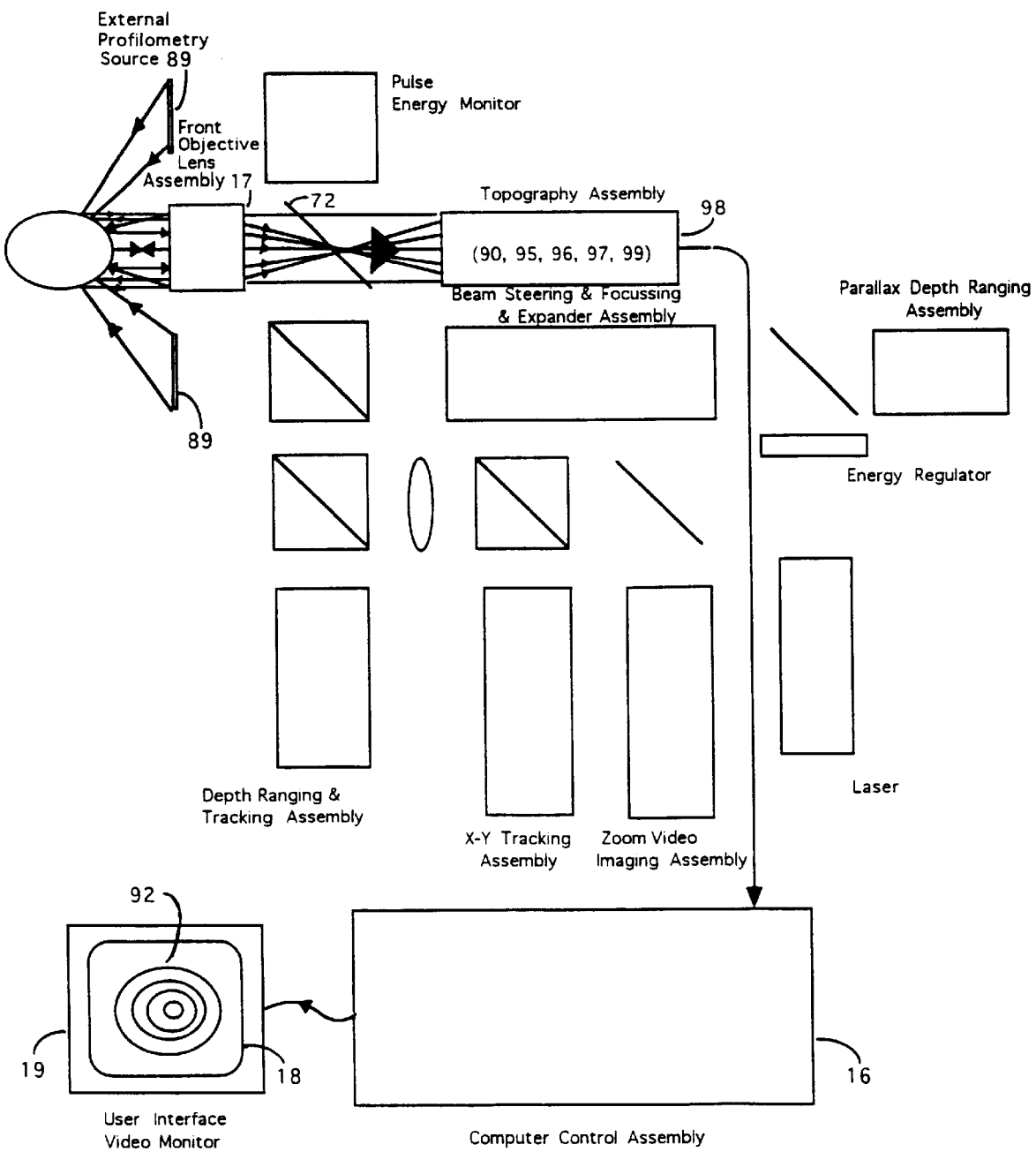
FIG. 7 is another block diagram indicating the light path between the topography assembly and the eye together with the control loop and interface with the video monitor display. The displays generated by the topography loop depicted in this Figure are overlayed the live image shown in FIG. 7 by the computer control assembly.

FIG. 7 shows the light path for the topography assembly 98, which provides a three-dimensional mapping system directed at the surface of the target, e.g., the eye of the patient. In a preferred embodiment of the system 10 (as described by Sklar in U.S. Pat. No. 5,054,907 and further extended by McMillan and Sklar in U.S. Pat. No. 5,170,193, all of which are incorporated herein by reference), the subassembly 98 may comprise a light projector 95 including an internal profilometry source 90, an illumination mask 96, an optical collection system 94 and a profilometry assembly consisting of, e.g., an adjustable aperture 99 and a CCD camera 97 equipped with a frame grabber, such as an array of dots arranged into rings and radial spokes converging to a common center, onto the tear layer of the eye. The reflected images of the predetermined pattern are collected by the optical assembly 94, which may include a set of plates to correct for any astigmatism induce by the tracking mirror 72 and any other interior mirrors, fed into the profilometer camera 97 through the aperture 99 for analysis. By controlling the angle of acceptance of the light bundle from each virtual image, the adjustable aperture acts as a spatial filter, providing a physical representation of the source of paraxial rays through trade-offs between resolution and brightness. The camera includes mans to digitize and electronically enhance the images. The signals are fed to a microprocessor which performs preliminary displacement analysis using software means (embedded within controller 16) based on mathematical morphological transformations as described by the '193 patent. The transformations comprise a solution of a set of coupled differential equations, whereby the local normals and curvature parameters are computed at each data point so that the surface can be computed to within the measurement accuracy, and subsequently displayed on the video screen 20. The methods of light projection and profilometry permit the system 10 to operate with low intensity light signals to enhance safety and patient comfort while extracting significant signal levels form the noise background.

In other embodiments of the profilometry assembly, alternative projection techniques may be utilized in place of or in addition to the mapping and projection means described above. In one embodiment, an external profilometry source 89, consisting of an array of LEDs projects a patter of dots onto the eye in a manner described by McMillan et al. in U.S. Pat. No. 5,283,598. In this embodiment, curvature measurements of the anterior surface of the cornea can be obtained extending up to 8 mm in diameter around the center. Other techniques based on off-axis illumination may utilize, e.g., a slit lamp illuminator 77 to obtain measurements of the thickness of the cornea, the depth of the anterior chamber and/or the thickness of the lens (the latter coupled with standard keratoscopy methods to correct for corneal curvature). Mounting the slit lamp at a fixed location relative to a CCD camera (such as 97) and rotating the entire structure around a center axis would also provide a method to collect global corneal data (out to the limbus) yet without sacrificing local accuracies, given the simultaneous 3D tracking capability already contained in the system. In this manner, the domain of topographic measurements can be extended from limbus to limbus while providing pachometry data as well. Alternatively, topography methods based on Ronchi grating in conjunction with Moire interferometry, or advanced holographic techniques as discussed by e.g., Varner (in *Holographic Nondestructive Testing*, Academic Press, New York, 1974 pp. 105) and by Bores (in "Proceedings of Ophthalmic Technologies," SPIE 1423, C. A. Puliafito, ed., pp. 28 (1991)) may be utilized in future embodiments of system 10, if warranted for specific interventions.

Figure 8:
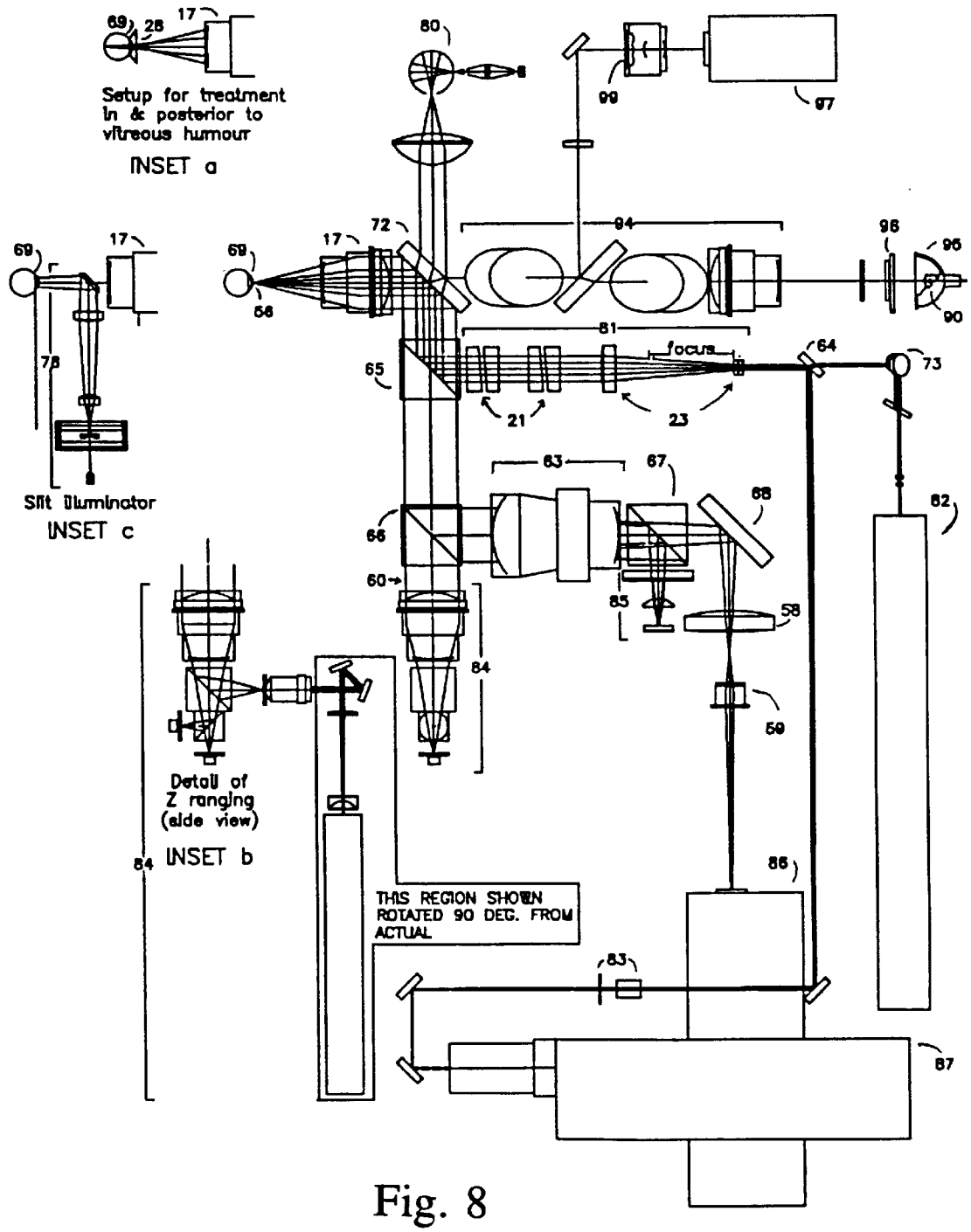
FIG. 8 is a scale drawing of one embodiment of the instrument of the present invention.

FIG. 8 is a schematic optical layout of a preferred system of optics for the instrument of the invention. In FIG. 8, a Schneider Cinelux Ultra 90 mm focal length f/2 lens is combined with a Schneider Tele-Xenar 360 mm focal length f/5.6 lens, matching conjugates to form a 4×/0.24 numerical aperture (N.A.) "objective lens" 17 with a working distance of 59 mm. This type of design embodies a key feature of the present invention, whereby a comfortable distance between the patient and the optics is implemented (sufficient to provide the surgeon/user enough open clear space to easily fit his hands between the front "objective lens" 17 and the patient's eye/target surface 69) while maximizing the aperture ratio of the system. A beam splitter between the front and back lenses of this "objective lens" allows the 90 mm lens to also serve as the final focusing lens for the laser. A Schneider Xenon f/2 lens, with 28 mm focal length, relays the image to the camera contained within subassembly 86, with magnifications zoomable from about 0.4×–5.4× in this embodiment of the invention. An appropriate field lens 58 is used to provide uniform illumination across the image of the maximum 15 mm field of view at the object (eye) and to reduce the magnification. Zooming can be accomplished by computer-and-stepped motions of both the zoom lens 59 and the camera. The total optical magnification is thus zoomable in this embodiment from about 0.8 to 11. With the image incident on a 2/3" video detector and displayed on a 13" (diagonal) monitor, an additional 19× video magnification is gained, thus a maximum magnification from the target to the screen of about 200× is achieved.

Another important feature of the optics of the system of the invention is that the servo tracking mirror 72 actually is positioned inside the "objective lens" assembly (the final element has been designed to have sufficient field to accommodate the small misalignments caused by the tracking mirror). This enables the system to achieve rapid tracking of ocular features (or other tissue features) in an efficient and relatively simple assembly, without moving an entire objective lens in following the sometimes rapidly moving features.

The optical system is designed without correction for the aberrations of the eye. For work in the cornea no corrections are needed. For work at image planes located posteriorly to the cornea, such as the retina, for example, contact lenses 28 (e.g., Goldman or similar) may be used, as shown in Inset a of FIG. 8.

As illustrated in FIG. 8, the illuminator light beam contained within assembly 82, first is reflected off a turning mirror 73, then transmitted through mirror 64, to join substantially coaxially with the path of the laser beam along the beam axis (see FIG. 2). Both beams are then steered through the beam steering and aiming optics in assembly 81 and are reflected off a reflective surface in the polarizing beam splitter 65 before being incident the tracking mirror 72. The polarizing beam splitter 65 (along with beam splitter 67) effectively prevent internal back reflections of the laser pulses from the optics of the system from damaging or overwhelming the sensitive video microscope camera contained in assembly 86.

Also indicated in FIG. 8 are the optical tracking and viewing elements, namely, depth ranging assembly 84, X-Y tracking assembly 85, and surgical microscope 86, all share the same optical path from beam splitter 66 to the eye. Some key design details of the Z-tracking assembly 84, including the illumination source (such as a red Ne—Ne laser) are shown in Insert b. These are described in more detail in U.S. Pat. No. 5,162,641.

As FIG. 8 shows, the beam generated by the therapeutic laser 86 and parallax ranger 82 are coaxial with each other, but the axis of these beams is not necessarily coaxial with the axis of view of the profilometer camera 97, the topography illumination source 90 or the other tracking/viewing assemblies 84, 85 and 86. This is because of directional steering Risley prism sets 21 embedded within assembly 81 which are outside the optical path of assemblies 84, 85 and 86, but within the optical path of the parallax depth ranger 82 and laser 87. The Risley prisms are steerable via the computerized control assembly 16 under the control of the surgeon/user through user interface commands. They provide means for adjusting about the X and Y axis, thus letting the physician select different locations for firing the laser, as disclosed by Fountain & Knopp in U.S. Pat. No. 5,391,165 (which claims priority from U.S. patent application Ser. No. 07/571,244). Elements 82 and 87, therefore, will only be coincident with the axis of view of depth tracking assembly 84 when the surgeon aims the laser directly at the center of the field of view of assembly 84. In other instances they will share the same "optical path" via elements 72 and 17, but they will not be on identical axes. The Risley prisms within assembly 81 allow movement of the actual aim of the therapeutic laser beam from laser 87 to a real aiming point which is coincident with the computer-generated aiming points.

The set of beam expander lenses 23 preferably are positioned as close as practical to final objective lens 17, and are initially adjusted so as to expand the diameter of the laser pulse emerging from the laser cavity and collimate it so that a parallel but expanded beam of light emerges from lens 22. The expanded, collimated beam is incident upon the final lens 17, and the expanded beam fills the lens to the extent compatible with vignetting for off-axis aiming thus, a large diameter beam is focused by lens 17, so that only at the point of focus within the eye is the diffraction limited pulsed laser beam effective in generating the desired therapeutic lesions in the eye. The depth of the focal point is varied by adjusting the distance between the two lenses 23, which has the effect of changing the degree of collimation and hence the focus as indicated explicitly in FIG. 8. the surgeon's adjustments of the focus of the beam via the computerized control system 16, are superimposed on top of the automatic adjustments effected by the tracking system, and net focus changes are carried out by the system. This is easily accomplished using hardware and software associated with the system which does not in itself form a part of the present invention.

The decoupling of the aiming and viewing functions allows off-axis work, which represents a major improvement in the function of the system 10, in that off-axis capability is a mandatory feature for corneal and most other applications. Thus, an independent mirror 68 is inserted upstream of assembly 86 to allow viewing, while aiming is performed independently in the coaxial illumination path using the Risley prisms 21 of subassembly 81. In an alternative embodiment of the system disclosed herein, a secondary angular steering mirror 60 (no explicitly shown in FIG. 8) may be added in assembly 84, to compensate for motion imparted by the X-Y tracking mirror which can, for large enough eye motions, cause the Z-tracking system to "lose lock."

Inset c of FIG. 8 shows some schematic detail of the external slit lamp illuminator, provided in an alternative embodiment of system 10 to augment and/or replace the internal profilometry illumination source 90, and provide ocular thickness measurements as was described above (see discussing following FIG. 7). The slit lamp constitutes the only element of the system not coaxial with the optical path defined by the tracking mirror 72 and the "objective lens" 17 common to all the other subassemblies.

Figure 9A:
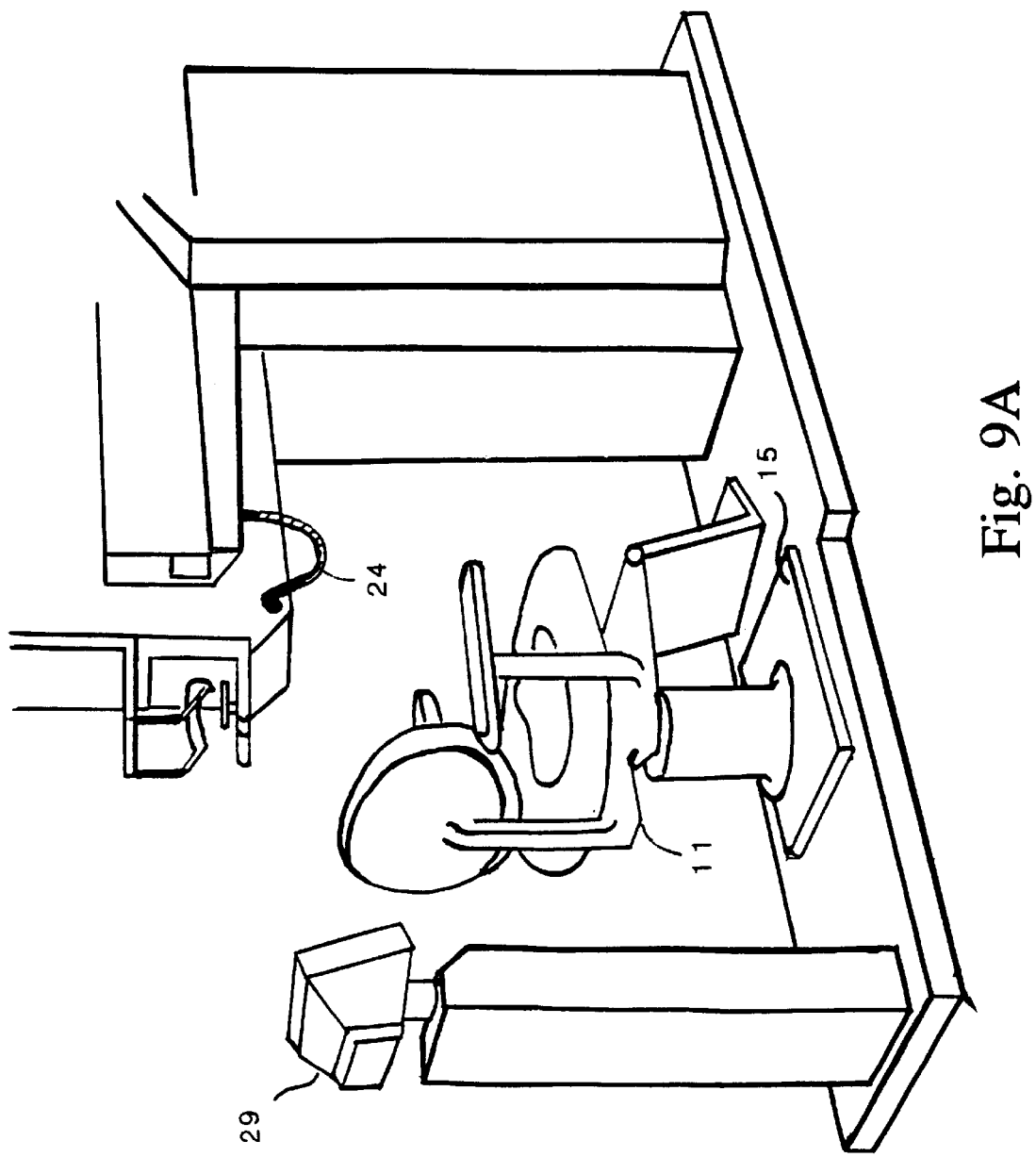
FIGS. 9a–9e represent three perspectives of an artistic rendition of an ergonomic configuration of the workstation. The system was designed to accommodate the engineering subassemblies in a maximally compact manner while providing a large amount of clear space for the patient.
Figure 9B:
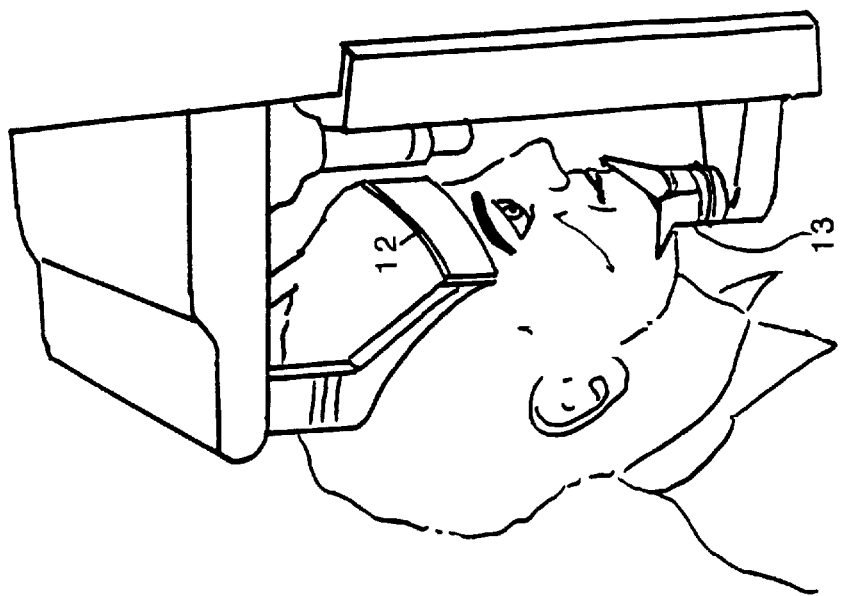
Figure 9C:
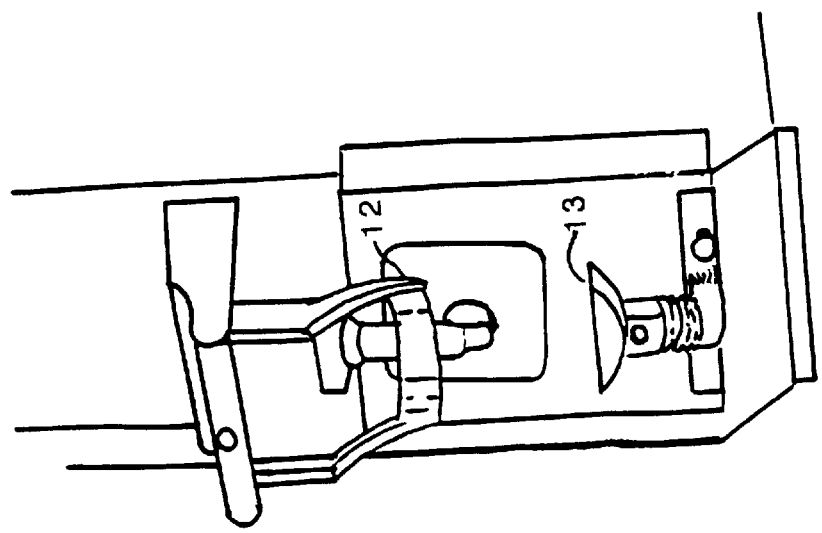
Figure 9D:
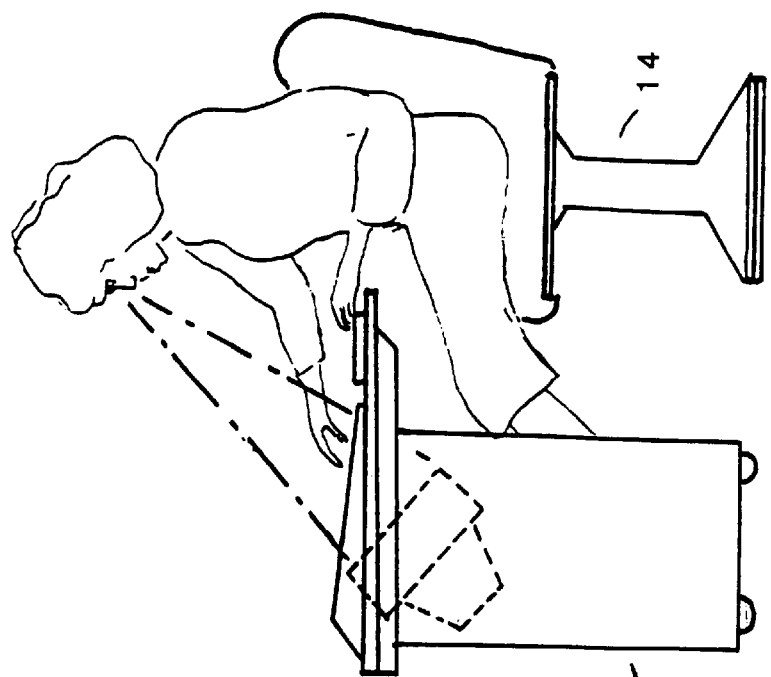
Figure 9E:
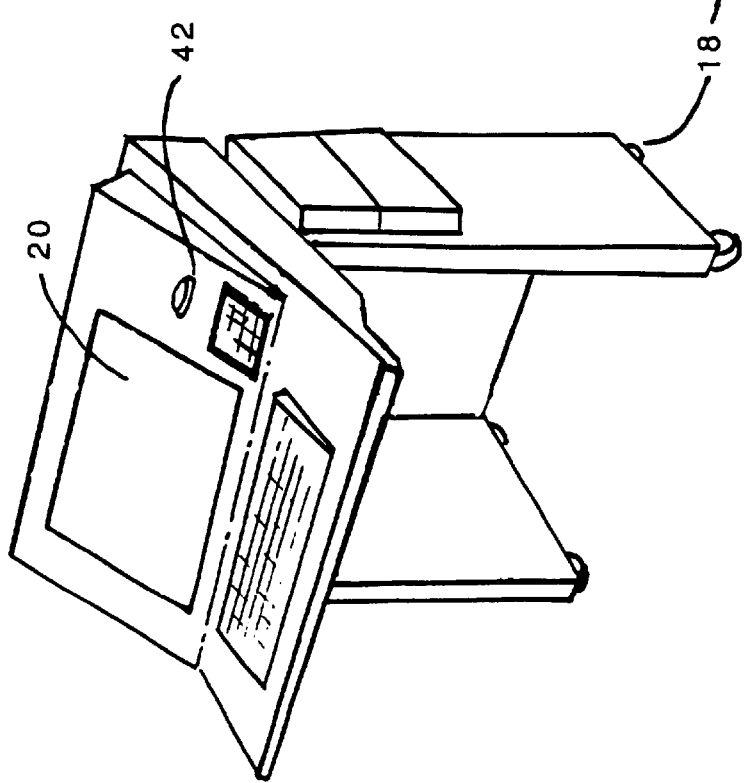

FIGS. 9a, 9b, and 9c show three perspectives of an ergonomic rendition of the workstation which incorporates the entire system 10. System 10 in this illustrated embodiment of the invention is intended for ophthalmic surgery, with the patient to be seated, as shown in FIG. 9a, in a chair 11 with his forehead against a forehead rest 12 and his chin against a chin rest 13, as shown in FIG. 9b. Both forehead and chin rests are fully adjustable. The surgeon/user is free to stand at a convenient location where he/she can survey the progress of the surgery as depicted on the video monitor means 18 (containing the video display means 27, including screen 20) as depicted in FIG. 9c, while having direct access and observation of the patient, or to sit in a chair 14. The seats 11 and 14 for the patient and the surgeon, respectively, preferably are fully adjustable with e.g., tracks 15 (shown in FIG. 9a) for adjusting proximity to the apparatus and with full height and seat back adjustability.

A hand held system control switch 24 in FIG. 9a may be provided for the surgeon/user as a safety device which will both enable the laser triggering means when sufficient pressure is exerted on device 20 (via a simple toggle switch, for example), or alternatively will immediately interrupt laser firing if pressure on the control means 24 is released.

Figure 10:
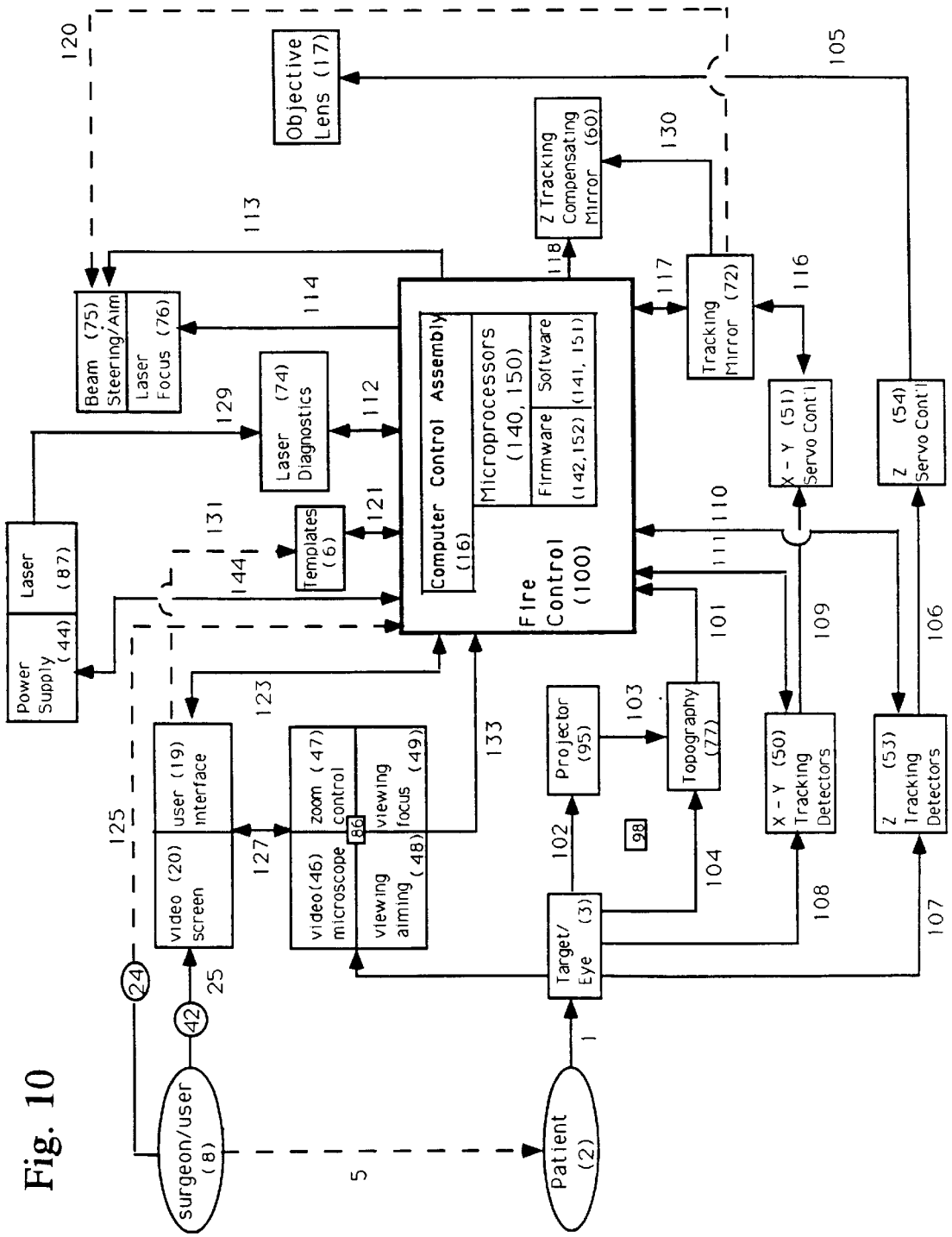
FIG. 10 is a detailed block diagram illustrating the functional interdependence among the various optical subsystems.

FIG. 10 is a functional block diagram showing the principal components and individual control and informational feedback functions of the precision laser surgery system of the invention, all indicated as being under control of a central processing computer 16, designed to integrate and control the operation of the entire system 10. The computer may include a microprocessor 140, software programs 141, and firmware 142, as indicated in FIG. 10, as well as a number of other control and indicate features (not indicated) such as the enabling (or disabling) of internal safety interrupts, a light-emitting diode (LED) display which indicates when the tracking system and target acquisition system are operational and on-target, an LED which lights up when the system components have successfully been verified to be performing within system specification ranges, an LED indicating power is on, and a dedicated video display function to assist in detecting location of a system malfunction. Note that some key functions in the system are carried through dedicated microprocessors 150, which, for simplicity, are shown in FIG. 10 sharing the same block as the central microprocessor 140.

During the start-up phase of system 10, a complete system verification is performed automatically without further prompting form the surgeon/user, including a set of internal diagnostics listing the status of operational use of the various assemblies. During this start-up phase, the assemblies shown in FIG. 10 (and FIG. 1) are each individually tested for operational status within prescribed tolerances. If all tolerance levels are satisfied, the user interface screen 20 appears and the system is enabled for use. Additional safety LEDs acknowledge sufficient pressure on the laser fire safety interlock in the hand-held (or, foot pedal) safety device 24, and whether the microprocessor generated template pattern is in control of the firing sequence.

As shown in FIG. 10, the central computer (which receives simultaneous diagnostic measurement and tracking information) closes each control loop through a central fire control function shown as block 100 forming a critical part of the computer control assembly 16. This fail-safe mechanism is a key feature provide within the instrument and system 10. Thus, the computer, which directly controls laser firing, as indicated by control line 144, automatically interrupts the firing sequence should any of the required operational specifications not be met (such as loss of tracking, deviation of the pulse energy, etc.). If all preset conditions are met, the computer control assembly enables and fires the surgical laser in accordance with preselected templates shown, functionally, as block 6. The required information comprises confirmation that the template is still positioned correctly, i.e., that the targeted feature of the eye has been tracked within a preselected time allotted, so that the images of the eye remain stabilized. If this confirmation is not sent (or a contrary signal could be sent signal that tracking is lost), the template controlled laser firing is immediately interrupted, as discussed in more detail below.

The user interface shown in a block 19 in FIG. 10, communicates with the central computer unit 16 as indicated by control line 123, though it may also have some controls which do not involve the main microprocessor 140. Thus, if the surgeon wishes to generate a template for surgery, as shown in dashed line 131, or merely to change the display on the video screen for the purpose of selecting a different type of presentation, or for imposing a different surgical path on the screen, these communications are carried out through the central processor unit (CPU) 140 (taken to include appropriate software 141 and firmware 142), which controls the computer-generated images (CGI) on the screen as well as most other functions in the system. As such, once the surgeon/user has finally determined his selection of template, has superimposed that template using the computer controls 16 onto the positioning diagnostics at the desired location where the surgery is to be effected, and the modifications to the shape of the template have been effected to accommodate for the particular configuration of the patient as observed through the video display means 27 (which includes screen 20) and the reconstructed target cross-sections, then the system is set to automatically fire at a discretized approximation of the configuration selected on the video screen 20. Discretization techniques, computer pattern overlay means, and the inherent CAD/CAM software techniques necessary to accomplish this process are known art and, as such, are not further described. The user's control of the template is thus indirect, proceeding via instructions received and stored in the computer memory, which in turn, generates, processes and stores template information as shown by control line 121.

The CPU 140 is connected to a number of other components. For example, it can send information to an I/O unite (not shown in FIG. 10) for record keeping. The transmissions may include, for example, patient history records to be printed or stored.

The CPU 140 can send control signals to a dedicated I/O boards 152 which may be used for e.g., driving motors associated with the steering Risley assembly 21, as well as for driving X-Y axis adjustments and other tracking functions through software included in 151. Commercially available dedicated I/O boards are capable of handling 16 analog channels and three digital channels in the currently described embodiment of the system 10. Thus, one board (in, e.g., 142) can handle diagnostic information relating to laser status, position status, tracker mirror status, and other diagnostics which may be implemented as needed such as intraocular temperature, intraocular pressure readings, and surface wave propagation measurements to enable calculation of the Young's modulus and other elasticity constants in an effort to determine applicable constitutive relations. The sensors for these conditions of the eye are not shown in the drawings, but can be incorporated in the system of the invention.

In FIG. 10, the surgeon/user is indicated at 8. Interaction between the surgeon and the patient is mostly indirect (as shown by dashed line 5), via the instrument and system of the invention. Thus, information and data concerning the patient's tissue is fed back, indirectly, through the instrument, to the surgeon, via video display 27, contained within user interface 19. The surgeon/user inputs instructions and commands to user interface 19 and the user interface feeds back information to the user, principally via video screen 20. This is indicated by a line 25.

The pointing device 42 is indicated in FIG. 10 as a key link in the surgeon's control of the user interface. It is used to control all aspects of the operation from generating templates to viewing, diagnosing and treating the target tissue.

The eye/target 3 is shown as sending information to a topography system 98 (comprising a light projector 95 and topographic data collection system 77), a viewing/imaging system 86 (comprising blocks 45 through 49), and to X-Y and Z position analysis tracking detectors 50 and 53 contained within assemblies 85 and 84, respectively. As represented in FIG. 10, the imaging/viewing system 86 comprises the video microscope 46, which presents the tissue video image (exemplified in FIGS. 12–15 discussed below), the zoom control 47, the aiming viewing means 48 and the focus viewing means 49. A double-ended arrow 127 indicates transmission of the video information to video display means 27, forming a part of the user interface 19, and resulting in live video images 4 on video screen 20. Control arrow 127 between the user interface and viewing system 86 also indicates that the surgeon may control the magnification of the video microscope depicted in block 46 via zoom control function 47, as well as view selected aim points and beam focus, all of which comprise parts of complete assembly 86.

The control line 123 from the user interface to the microprocessor (which indicates the surgeon/user's selections made by input controls other than touch screen), thus serves to represent another user input to the microprocessor 140 active when the user steers the field of vision and the aim of the laser. Such deliberate control by the surgeon will indirectly control the laser beam aiming and focus via the microprocessor (along the control lines 113 and 114, as discussed below). User interface signals to the computer control are also used by the CPU 140 to adjust the CGIs accordingly, reflecting precisely the desired change in beam focus, image magnification and aim points.

The content of signals sent by the microprocessor (CPU) 140 to the video screen (along control line 123) relate also to the computer-generated topographical images acquired as shown by line 101 from topography system 98, and discussed further below. CPU 140 also controls the display of the branching look-up tables 30 shown on screen 20, as well as other pull-down menus, displays and other pertinent information.

In FIG. 10, information about eye 3 is shown as being sent to a block 77 labeled Topography via control line 104. Arrow 102 indicated the derivation of such information from the eye via the projection system 95 while the transformation and processing of said information by the topography system 77 is represented by arrow 103. An information control line 101 indicates processing and feedback via the computer control assembly 16 and dedicated microprocessors contained in 150. Block 77 is taken to include the sensors, CCD cameras, such as profilometer camera 97, optical collection assembly 94, aperture 99 and analysis loops. As represented in FIG. 10, the functions of a dedicated microprocessor and programming for this subsystem are included within blocks 150 and 151, respectively. The derived information relating to the topography of the eye tissues is then sent to the tracking stabilization blocks discussed next.

The X-Y position analysis and tracking system (contained within assembly 85 and described operationally for FIG. 5) proceeds primarily through the tracking detectors 50 and the servo drive 51, but is also understood to include the servo logic loops and any associated optics required to steer the light emanating from the images received from target/eye 3, as indicated by arrow 108, for the said purpose of detecting and following any movement of the patient's tissue. This information is related to the X-Y servo drive 51, via information control loop 109 which, in turn, controls the tracking mirror 72, as indicated by arrow 116. This logic sequence indicates that the detectors subsystem, after analyzing the images and determining that a feature has moved, sends information or instructions to the servo drive, which constitutes the target tracking assembly (along with dedicated processors included in 150). The information or instructions can comprise new coordinates for the position of mirror 72. The target tracking assembly thus translates the new coordinates into instructions for the mirror drivers via arrow 116 to the servo mirror 72), which instructions may include coordinate transform information and commands for the tracking mirror 72 to turn to a new angle which will again be centered on the same features.

An information arrow 111, shown between the position analysis tracking detectors and the computer control 16, indicates processing of the information and stabilization of the video images by a dedicated microprocessor, contained within the units 150, shown in FIG. 10 (for simplicity) as embedded within the central computer assembly 16. Computer processing functions relating to the X-Y tracking unit include appropriate programming units which are able to analyze data taken by the tracking detectors 50 and to determine form the data when features have moved and to relocate those features and calculate new coordinates for mirror position. Some of these functions were described further with reference to FIG. 5. Control arrow 117 also represents feedback from the mirror assemblies as to their actual position, as well as confirmation that the mirror was physically moved, i.e., that the instruction to the mirror resulted, where indicated, in a physical displacement. If this move does not occur, the system loops back to the target tracking assembly which sends a signal along control loop 144 to disable the laser firing. The important control arrow 144 thus relates to the preferred safety feature embodied within the present invention. The target tracking assembly, if unable to track the moved feature to a new location within the time allotted (which may be as fast as a few milliseconds in a preferred embodiment), will send an instruction to an internal fire control 100 to abort firing of the laser, and this command is relayed to the laser power control via arrow 144. The automatic firing control mechanism represented by block 100 will also interrupt the execution of the template program, vis a vis the control line 121 in FIG. 10. The interrupt preferably lasts only until the feature is recovered via the tracking loop (discussed above), if in fact the feature is recovered.

Examples of tracking loss not associated with the logic loop are failure of the signal to be effected by the servo drivers, required mirror motion exceeding the limiting displacement of the servo driven actuators and malfunction of the drivers or slides. Safety controls which shut down the operation of the system whenever tracking is lost are a feature of the present embodiment of the invention but are not further described as they comprise standard safety devices known in the field.

In one embodiment of the invention, a microprocessor in block 150 also controls the tracking mirror or servo mirror 72, as indicated by arrow 117. The microprocessor controls the mirror in response to input from the tracking detectors 50 in conjunction with suitable programming firmware and software 152 and 151, respectively. Thus, once the tracking detectors input signals to the microprocessor (via control line 111) which indicate that the subject tissue has undergone movement, the microprocessor handles the position analysis and the target tracking (mirror instruction) and outputs as signal in response to the results of the tracking to the tracking mirror 72 as indicated by line 17.

A dashed control 120 from servo tracking mirror 72 to laser aim block 75 indicates that the laser aim is steered along with the X-Y tracking (as discussed in reference to FIG. 4). In a preferred embodiment, there may be an additional control line (not shown in FIG. 10) from the tracking mirror to the viewing assembly 86 to allow for the fact that since the laser and surgical microscope lines of sight are not coaxial, the field of tissue being viewed and the laser are always decoupled.

It is noted that the dedicated microprocessor or other logic unit having the capability of carrying out the logic sequence needed for pattern recognition, coordinate transform analysis and generating instructions to the mirror drivers to appropriately adjust the X-Y position of the mirror 72 can also be included within the servo drive 51, in which case the function of the separate control arrow 11 is obviated.

Similarly, the Z-tracking detectors 53 (contained within the depth tracking assembly 84 discussed earlier in connection with FIG. 3) send commands regarding viewing depth and beam focus to a Z servo drive via control loop 106, which in turn relays the information to the final focusing lens 17 via information loop 105. In a preferred embodiment of the invention, the change in orientation of the tracking mirror 72 is communicated to the Z-tracking compensator mirror 60 via control loop 130. This feature is provided to maintain the focus of the Z-tracking system on the instantaneous vertex of the cornea, as discussed above with reference to FIG. 8.

We note that the final focusing lens also forms a part of the imaging system 86, in the sense that the surgical microscope receives light on a path which passes through this lens 17, and the focus of the imaging is adjustable at 48 and 49 by the surgeon/user; consequently, no separate control line leading from the objective lens to the viewing assembly is indicated in FIG. 10.

The user interface activated laser fire control is shown by line 144 with arrowhead toward block 44 representing an internal laser fire control mechanism which turns on the power source 44 that acts as the driver for the therapeutic laser 87. The fire control sequence is initiated by the surgeon/user when clicking the mouse 42 which moves a cursor across the video screen. Firing can be manually interrupted by pushing the "abort" button 24, provided as an additional safety feature that is under control of the surgeon/user as indicated in FIG. 10 by dashed line 125.

When operating, a fraction of the beam passes through a laser diagnostic assembly 74, as shown by control line 129 which serves the purpose of monitoring the laser pulse energy to insure it is performing to specification. The information is relayed to the central computer unit 16 to be analyzed and compared with specific parameters, as indicated by line 112.

The laser beam also passes through the steering and aiming subassemblies shown as blocks 75 and 76 (contained within subassembly 81). The steering assembly 75 includes the Risley prisms, which are not under the direct control of the surgeon. The beam focusing assembly includes beam expander 22, which is likewise not under the direct control of the surgeon. Note that the entire beam steering, aiming and positioning loop also includes the front objective element 17 as was discussed vis-à-vis FIG. 4. So, again there is no separate control indicated between the objective lens and the beam steering and focusing blocks 75 and 76. Instead, these subsystems are shown as receiving direct control instructions form the central microprocessor via control lines 113 and 114 (which include indirect information relayed through the tracking mirror 72 and objective lens 17, both of which are adjusted via appropriate servo drives whenever the patient's target tissue moves).

Finally, the dashed line 5 indicates the laser beam's action on the target, i.e., the patient; the actual laser treatment is thus only indirectly controlled by the surgeon/user.

FIG. 11 shows again separate functional blocks for the target viewing assembly, the target tracking assembly, the topography assembly, the beam positioning/aiming assembly and the fire control, all shown now as being activated by the user interface, which is in turn manipulated by the surgeon/user through a suitable pointing device 42 also indicated in FIG. 11. The operator/user interface interaction takes place primarily through the video screen means 20 (and associated elements such as the pointing device 42) as indicated by control line 25, while central microprocessor control of the interface is shown by line 123. The user interface 19 comprises for the most part an "intelligent" menu of options available to the surgeon, the video screen 20 which displays the options in a suitable number of modules, the pointing device 42 (such as a mouse, joystick, trackball, light pen, etc.) for making selections from the menu, the fire control (or "abort") button 24 and various other buttons and numerical displays as were indicated in FIG. 9c in front of the surgeon/user. Aside from the safety feature indicators discussed previously, the trackball 42 (or other pointing device, as mentioned above) enables the surgeon/user to control and select from among the various software options available for a given mode of operation. Rotation of the trackball controls the position of a cursor on the video screen. A button next to the ball enables special features on the screen and allows the user to superimpose the proposed therapy on the video generated images of the target tissue. In the present invention, commercially available computer graphics software packages form a portion of the basis for providing the surgeon/user access to defining surgical templates. Other buttons allow the surgeon/user to switch from selecting previously defined templates, to modifying or creating new templates.

With the user interface, the surgeon is able to make selections as to types of surgery or templates to be used in the surgery, to view different portions of the tissue, to aim the laser, including the depth at which the laser fires, and to fire the laser to execute a pre-programmed sequence of firings. It also enables the surgeon/user to interrupt the procedure at any time. The surgeon makes his selections by moving a cursor across a Windows menu consisting of several modules each containing a number of options that can be displayed in the form of a branching look-up table 30 and pull-down menus. The cursor is manipulated, preferably by (in order to obviate the risks of miskeying on a keyboard) the pointing device 42 alluded to above. The symbols in the menu will include the type of display desired for the screen as shown in the examples displayed in FIGS. 12–15; selection of templates from among pre-programmed patterns for the proposed surgical procedure; other surgical parameters such as the laser pulse power level or the repetition rate of the laser beam; the beginning and ending diopter power of the corneal "lens" or, more generally, the optical prescription; the shape of the lesions; modifications of the templates or creation of new templates, memory storage and retrieval of information; record keeping and access to patient history files; access to statistical information about the likely outcome of a proposed surgical procedure; a selection of levels within the eye for which information is desired for a given surgical procedure; and others.

All of the above operational functions are created through software programming, the details of which do not in themselves form a part of the invention and are within the skill of the programmer.

Figure 11:
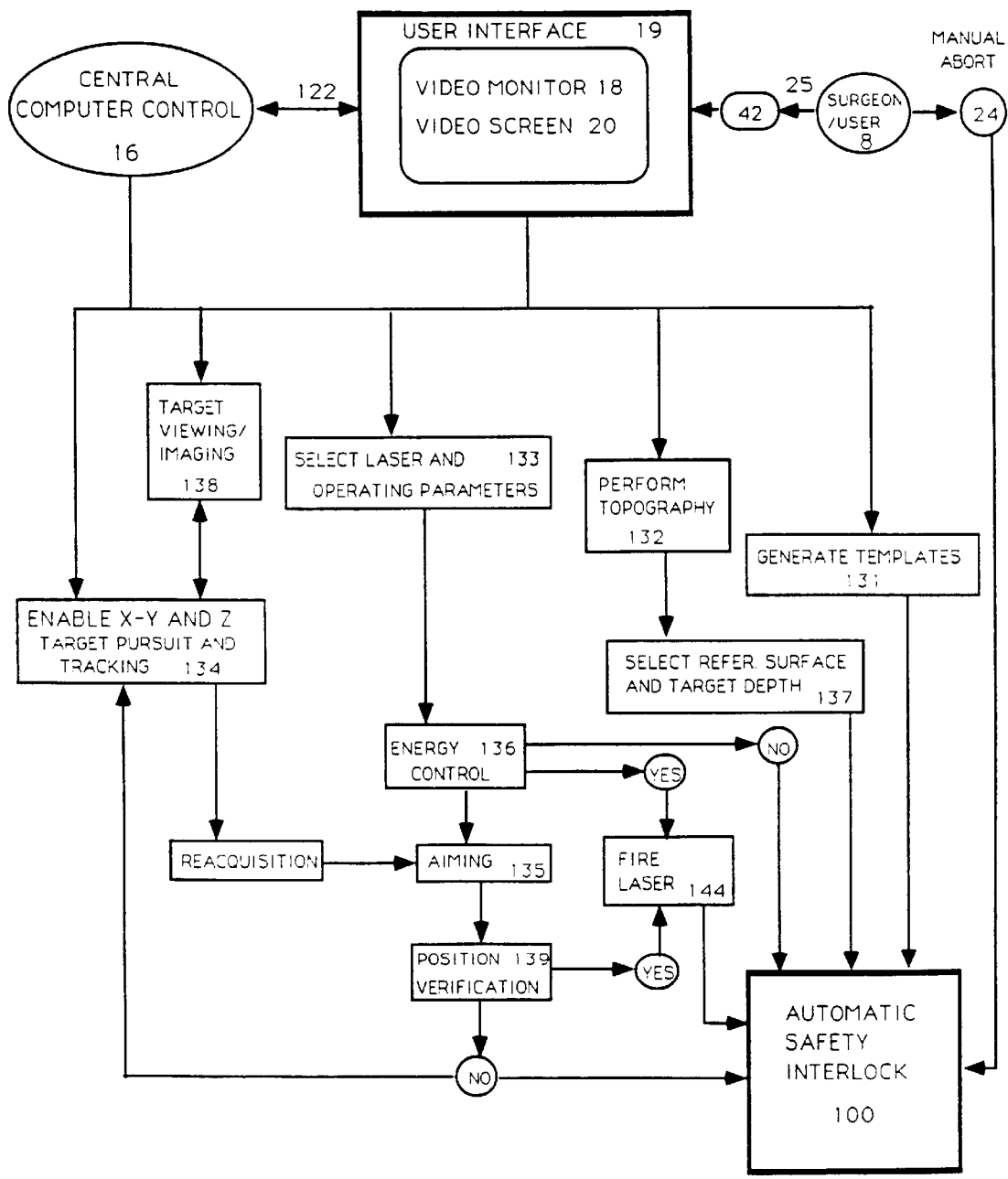
FIG. 11 is a block diagram showing the sequence of control and information flow from the user interface elements to the firing of the laser.
Figure 12:
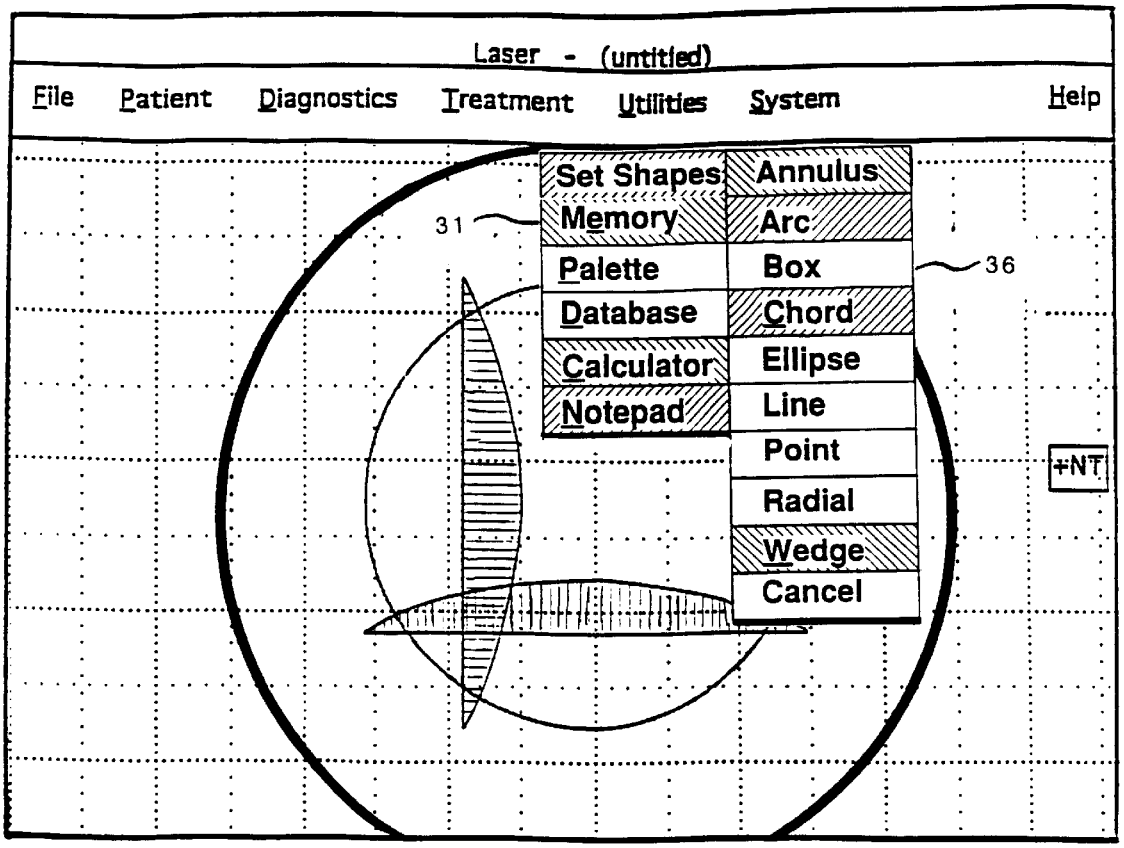
FIG. 12 is a photograph of a user interface screen showing a selection of computer-generated patterns which can further be modified using "CAD/CAM-like" editing functions, such as are contained in a "utilities" module.

As shown in FIG. 11, the surgeon/user starts the procedure by generating a template (or a set of templates), a function indicated in block 131. Based on a set of pre-programming patterns, the patient's optical prescription or—in the case of controlled animal studies—actual templates for the proposed procedure (derived from other previous surgeries conducted by himself or by other surgeon and stored in memory), means are provided for the surgeon to create a new template or modify an old template by appropriate resizing and resealing. The list of pre-stored patterns may include geometric shapes such as annuli, arcs, boxes, ellipses, radii, and others, as shown in the pull-down menu 36 of FIG. 12, under the "utilities" module 31. Specific types of operations and/or lesions may be selected from among options stored under the "treatment" module shown as vertical box 37 in FIG. 13. For example, in the case of corneal surgery, the starting point for generating templates for a particular eye segment may consist of selection from among a collection of relevant lesions, such as tangential (T-cut) or, for radial keratotomy, radial (2-rad, 4-rad, etc.), as illustrated in vertical box 38 of FIG. 13. Different sets of patterns are provided for e.g., cataract surgery, posterior eye segment surgery, or other forms of intervention for which the system of the present invention is deemed appropriate. Specific shapes of lesions can therefore be selected by the surgeon such as, e.g., the screens as shown in FIGS. 12 and 14 for corneal surgery, or a different set of screens for cataract surgery, or yet a different set of screens for posterior eye segment procedures. In a preferred embodiment of the display, templates are drawn on the screen in three-dimensions through selection from several standard geometrical shapes as shown in FIG. 12. Alternatively, a free form option may be included to allow the surgeon/user to draw arbitrary shapes as may be appropriate for certain types of surgical procedures. Selection of a treatment plane can also be done through, e.g., an "orientation" menu, indicated in box 37 of FIG. 13, under the "treatment" module. The selected patterns can then be used as depicted or, if a closed curve is indicated, filled in automatically according to the prescribed distance between firing locations as indicated in the menu selection under e.g., the "set parameters" box 39 illustrated in FIG. 14, and contained in the "treatment" module 37 depicted in FIG. 13.

The patterns selected are superimposed on a grid, shown on the screen, with spacings corresponding to appropriate dimensions within the eye. For example, in the case of corneal surgery, a 10×10 grid with 1 mm spacings would adequately describe the human cornea (which has a diameter of 12 mm). The areas between the grid points are transparent to the treatment beam.

When pre-programmed templates of the surgical path to be followed are used, such as in controlled animal studies, the surgeon has access to the same options as indicated above, in addition to superimposing directly the template on the screen over the ocular tissues.

Access to magnification is provided throughout the template selection and diagnostics phase through a zoom option, located on the screen. This function is within the domain of the viewing/imaging assembly and is indicated as block 138 in FIG. 11. The surgeon can thus view any desired segment of the treated area and/or the shape of the proposed lesions, at varying magnifications up to the limit imposed by the hardware.

Figure 15:
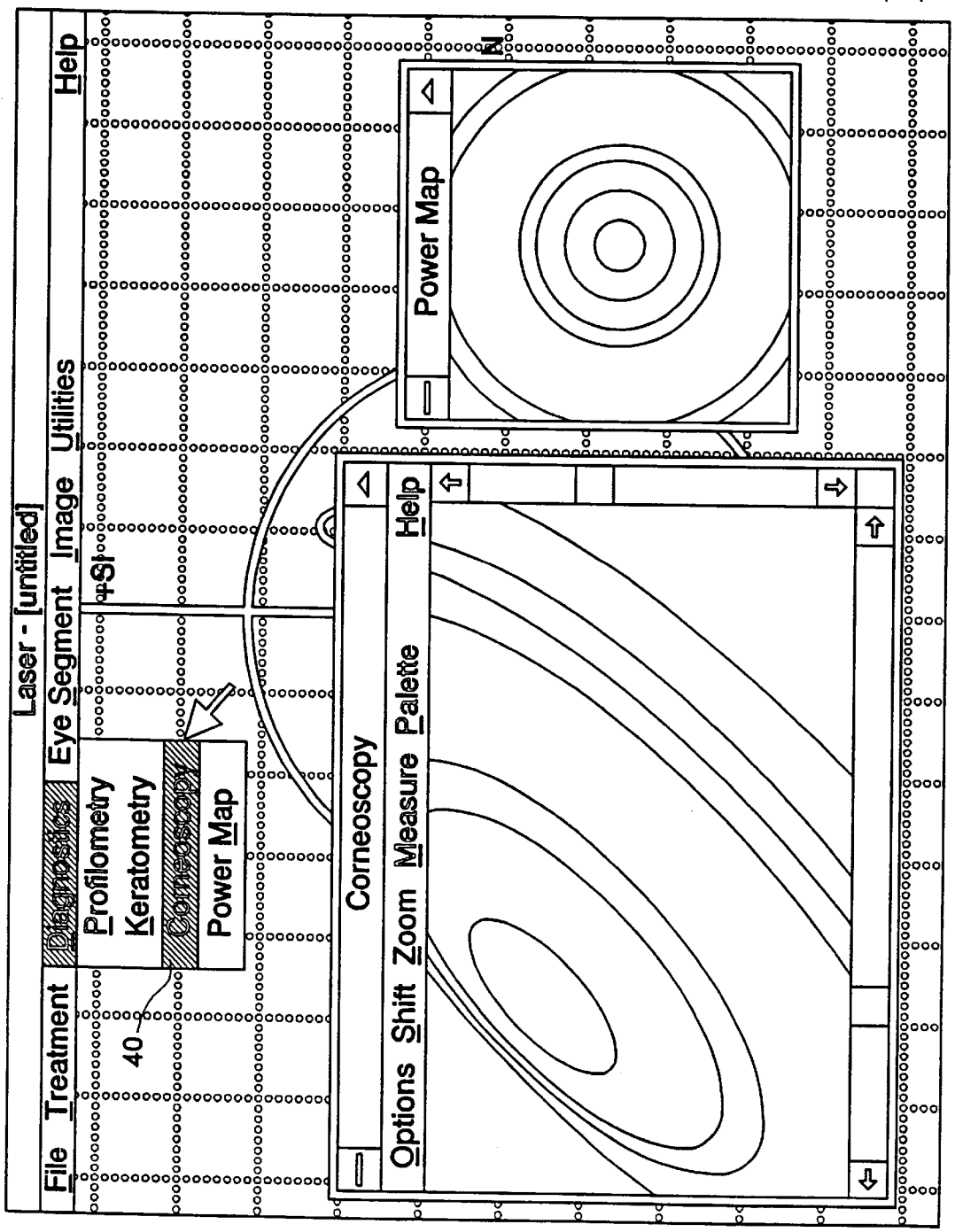
FIG. 15 is a topographical representation of a three-dimensional eye surface as seen from the user/interface screen, highlighting a sample "diagnostic" module.

The first step in the surgical procedure involves patient eye diagnostics, including key topographic measurements such a provided by profilometry, keratometry, and corneoscopy as indicated by block 132 of FIG. 11. A "diagnostic" module may be provided in a preferred embodiment of the user interface, an example of which is shown in FIG. 15. This module may comprise commands to perform various non-invasive procedures and present the results in the form of three-dimensional graphics and refractive power maps. Controls of the viewing system and the tools for performing measurements may all be exercised concurrently within this module. Thus, profilometry measurements, which involve the topography subassembly 98, provide the surgeon with data on the patient's corneal surface. The procedure involves projection of a pre-selected pattern unto the eye or other alternative techniques as was discussed for FIG. 7.

In a preferred embodiment of the invention, the 16-spoke, 5-ring pattern shown in FIGS. 12 and 14, has been selected, although other patterns may be appropriate for different procedures. The reflected images are grabbed, digitized and spatially transformed to reproduce key surface characteristics, which are saved as a file on a disk. The keratometry means reads from the file to generate a 3D surface that can be displayed on the screen in the form of a contour map as part of the corneoscopy routine, once the appropriate radii and planes have been selected. An example of such a power map is also shown in FIG. 15. In one embodiment of the software, a 75×75 matrix is used to generate the surface projection, in the form of e.g., an equi-power map 92. The 3D pattern can be manipulated by means of a scroll bar to rotate and tilt it. It can also be displayed in the form of a color coded contour map as visual aid to indicate feature elevation. A palette is provided in the menu under e.g., the "utilities" module to allow color selection for the display.

Based upon the corneal measurements, the spatial map of the refractive power of the cornea can also be constructed. This may also be included in the diagnostics module, and the power map can be presented in a separate window, if desired.

As discussed above, FIGS. 12–15 show examples of what may be displayed on a screen 20 of the video monitor 18. The information on the screen 20 is intended to give the user a full range of information regarding the three-dimensional structure or features of the particular tissues on which laser surgical procedures are to be performed. In a preferred embodiment of the user interface, some symbols are included on the screen such a in vertical strips 31, 36, 37, 38, 39, and 40 as shown on the screens of FIGS. 12, 13, 14, and 15. These symbols comprise a menu of selections for the surgeon/user. Other display means can be also used to present data in a more easily understood manner to the surgeon/user. For example, in FIG. 15, a preferred embodiment of the graphical representation means 92 or the topographical map means 93, is shown in a super-posed manner. These can also be shown as separate windows. The menu 40, shown in FIG. 13, may be used to generate on the video screen to show pertinent measurement data relating to the tissue on which surgery is to be performed. A final selection of the reference surface at a given target depth can be made concurrently with the diagnostic routine, by entering appropriate data in box 39 of FIG. 14 (which corresponds, in the example of FIG. 13, to the "set parameters" menu, shown as part of the "treatment" module 37) and observing the immediate effect on the reconstructed corneal surface, displayed in a manner similar to the example shown in FIG. 15. This type of corneoscopy display provides critical aid to the surgeon in determining, e.g., the degree of astigmatism present in the patient's tissue. In the preferred embodiment, the user will also be able to superimpose the template of the selected surgical path on the video microscope-generated image of the corneal (or other tissue).

A key step in the treatment involves selection of laser operating parameters for the actual surgery, indicated by block 133 in FIG. 11 and illustrated in the photograph of the user interface, as depicted in box 39 of FIG. 14. The principal parameters included in the treatment module may include the energy of the laser, the repetition rate, desired spacing between fire points, desired lesion depth and thickness (for the surface selected earlier), direction of treatment along the Z-axis (inward, outward), lesion radius for selected profile projections, and other pertinent parameters as may be indicated by a particular type of surgery to be performed. FIGS. 12 and 14 also show examples of what may be indicated on the screen for a selected corneal lesion shape which is shown in two projections, customarily referred to as S–1 (superior-inferior) and N-T (nasaltemporal). In a preferred embodiment o the elements included in system 10, the maximum energy/pulse is 0.3 mJ, in which case the spacing has a default value of 14 µm, as determined by the bubble size for that level of energy at that particular wavelength. These parameters are relevant to corneal procedures; appropriate laser parameters must be selected for alternate ophthalmic procedures, such as operations on the lens, for which the hardware of present invention can also be suitably modified.

The surgeon can thus use the information provided in the various windows to provide diagnostic information of the actual condition of the target tissue to the surgeon/user. Thus, the surgeon might first establish the pattern in the screen in plane view, observe the results of his selection in various perspective views, as shown in FIGS. 12 and 14, wherein the proposed lesion is automatically indicated, and reflect upon the likely outcome of the surgery with the ability to edit, an alter as desired, the designated template pattern prior to initiating the procedure.

Figure 13:
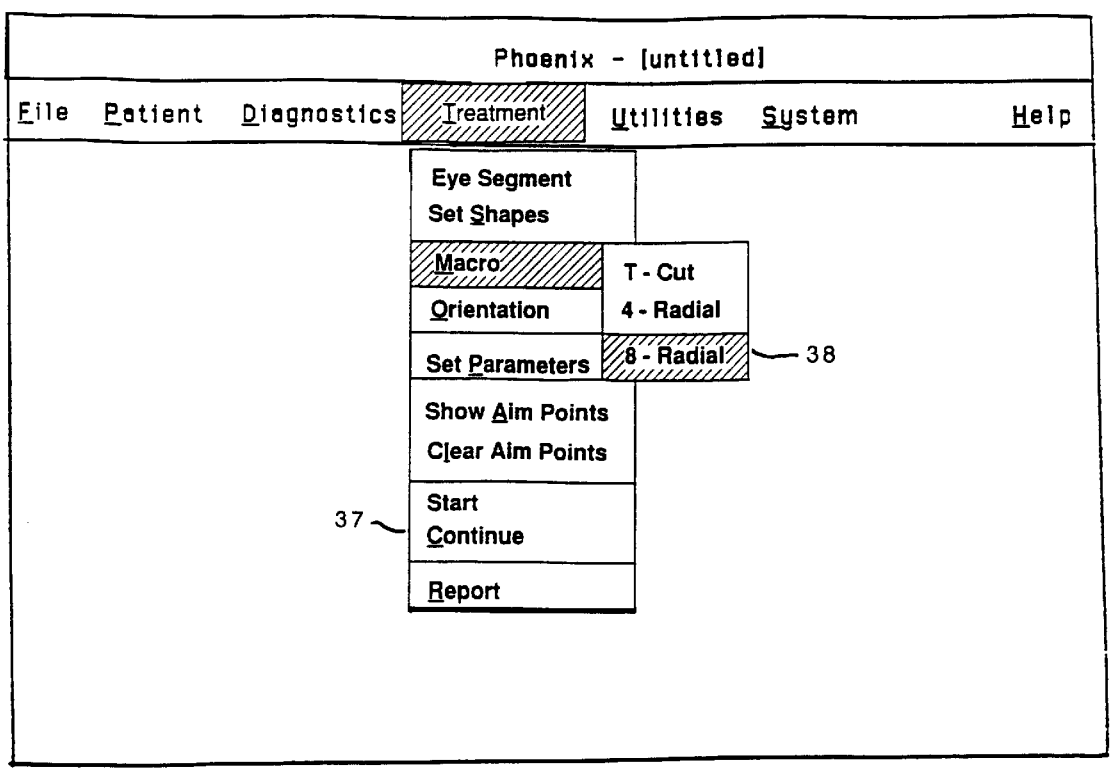
FIG. 13 is an illustration of a user interface screen showing a window of a sample "treatment" menu used to select treatment eye segments, set lesion shapes, choose operating parameters corresponding to the template designated procedure or other functions.
Figure 14:
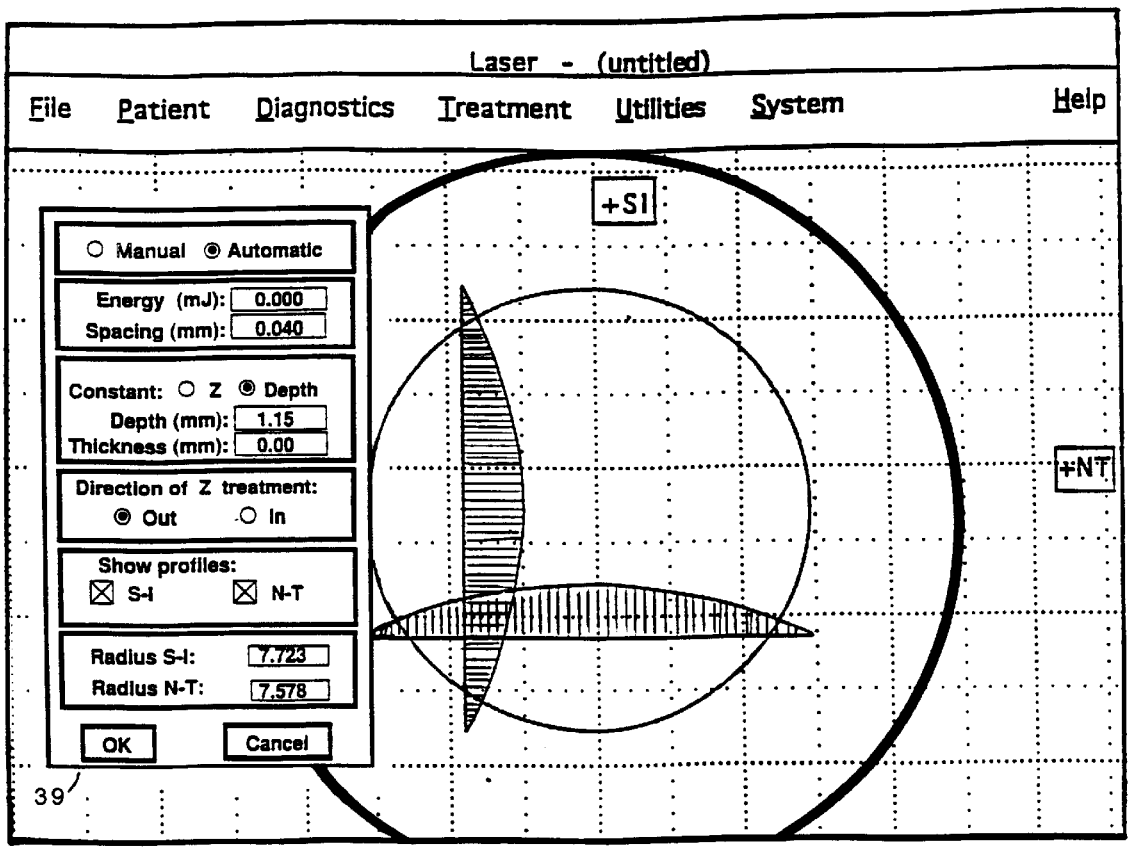
FIG. 14 is a photograph showing the same sample templates as FIG. 12, and highlighting an example of a pull-down "set parameters" menu.

At any point during the diagnostics and the lesion selection phase, the user can superpose the actual laser aim points on the proposed lesion shapes and/or image of the tissue (from the video camera) indicated on the screen through a click of the mouse, on the "show aim points" option from, e.g., the "treatment" module, box 37 in FIG. 13. This option is also activated just prior to the final step in the procedure, which involves actual firing of the laser to perform the surgery, as indicated by block 144 in FIG. 11.

The template-controlled laser firing must occur precisely in accordance with the pre-selected targeting sequence. It is the tracking system (including diagnostic, tracking and mirror movement) which is the critical link in this feedback loop. This function is indicated by block 134 in FIG. 11. The tracking feature is automatically activated during diagnostic and treatment phases. As noted earlier in this disclosure, if the tracking subsystem fails to move the servo controlled turning mirrors to maintain the target within acceptable error tolerances, then the template-controlled laser firing will be disabled until the images are again reacquired or until the surgeon re-initiates the program. Likewise, if an obstruction (such as a blinking eyelid for ophthalmic procedures or transient debris in industrial procedures) were to interfere with the imaging/tracking light path (which also corresponds with the laser beam path), the template-controlled laser firing will be interrupted until the images are reacquired and the appropriate position in the template firing sequence is recovered. The closed loop 135 indicates automatic aim point maintenance for the laser. If all conditions are met (patient ready, tracking is online, laser is armed), the surgeon may select the "start" option under the "treatment" module 37 (see FIG. 13) which commences the surgery. If, at any time loss of tracking is indicated, or other, potentially unsafe conditions are encountered (such as energy deviation, per, e.g., block 136 in FIG. 11), the firing sequence is automatically immobilized through safety interlock features shown as block 100 in FIG. 11 (see also FIG. 10). The surgeon can also choose to interrupt the procedure manually by pressing on the fire control or, abort switch 24, also connected to the safety interlock system. In either case, the last aim point position is stored in the computer memory, along with all other pertinent data concerning the operation. The procedure can therefore be resumed at will by clicking a "continue" option (also shown in box 37 of FIG. 13). This has the effect of allowing the target area to be reacquired and tracked, and the laser will then fire according to the original pattern and sequence selected, starting at the precise aim point location last exercised prior to the interruption.

Upon completion of the operation, a "report" option (see, e.g., box 37 in FIG. 13) may be provided, whereby the procedure details can be summarized and pertinent statistical information stored and displayed. A "statistical" module (not shown) may be provided as part of the software (e.g., under the "file" module) to fulfill this function. Characteristics of the treatment which may be recorded and reported may include the total number of laser pulses fired, the total energy deposited into the tissue, time elapsed and other pertinent data.

A disc file input/output (I/O) module is also incorporated to support all the necessary exchanges with external memory devices. Thus all the information about a given surgical session can be stored for future analysis and/or reports, along with the values selected for all parameters, templates, and personal data. The results of the profilometric measurements can be stored in a separate file, which may be retrieved when needed.

Note that the techniques for obtaining mapping and profile information of selected surfaces within the eye in the embodiments of the present invention are not limited to any one specific surface. The techniques described herein apply to either the cornea or the iris, lens, etc. With some modification in the imaging optics, retinal procedures may be included as well (note that the retina is a reflecting surface in that there is an index of refraction change across the surface. Consequently, there will be for each incident light ray a reflected ray, a refracted ray, ray absorption, and scattering of light, all of which must be taken into account when selecting specific methods for acquiring and interpreting data).

It should also be understood that the system of the invention is useful to the surgeon as a diagnostic and analytical tool, aside from its uses in actual surgery. The system provides for the doctor highly stabilized images of the patient's tissue—particularly the ocular tissue—not achievable with instruments prior to this invention. The doctor is given a display of the tissues, along with simultaneous tracking and stabilization. The invention therefore gives the doctor a very important tool in analysis and diagnosis of a patient's condition, and the invention should be understood to encompass the system as described even without the surgical laser beam itself. The system, with its computer-generated images (CGIs) on the display screen as well as direct video microscopic images displays of the patient/target, gives the doctor a means of visualizing the eye condition, as a replacement for the doctor's directly looking at the target tissues. The Template-Controlled Surgical Laser (or, Ophthalmic Surgical Workstation) invention should be considered as including the user interface, the computer and memory storage device relative to creating, modifying, storing, and executing surgical template programs. This assembly is defined in greater detail by Sklar in U.S. patent application Ser. No. 475,657 (now abandoned) which is incorporated herein by reference.

In the user interface, a video screen is provided in front of the surgeon, and the screen may even be divided into four quadrants: one quadrant showing an image of cell walls in real time taken from a video camera based, zooming surgical microscope which may be capable of enlargement from 25 times to 500 times, for example. The surgical microscope image might show a region having a dimension of as small as the order of 100 microns, for example. This real-time video image is of tissue at the precise location and depth at which the surgical laser is currently directed, or, in the alternative, of critical cells directly posterior to the target which should be monitored to help assure no damage to these sensitive tissues (e.g., corneal endothelial cells posterior to, but along the optical axis of, a laser pulse). The surgical microscope may be used to scan different regions at different depths under the control of the surgeon/user, even though the laser is not yet being fired.

The tracking subsystem of the invention serves two important purposes—it tracks and follows in real time (virtually "real time", i.e. delayed only by the speed of the electronics and the tracking mirror) the movements of the patient's tissue, not only the voluntary movements which can be damped with specialized treatment, but also the involuntary movements which are more difficult to control on a living specimen) and continuously re-presents an image of the same section of tissue at a closed loop speed equivalent to real time. Thus the surgeon/user is provided a continuous, substantially immobilized view of that tissue regardless of patient movements; and it further provides a fail-safe means for immediately stopping the action of the surgical laser beam in the event the tracking is lost, i.e. the tissue is not recognized by the computer stored image on which the tracking algorithm is following the motion, and the vision is not re-aimed at the appropriate tissue within the selected operating interval.

Continuously updated images, preferably video images, are presented to the surgeon/user as the surgery progresses, and these images contain all information, in three dimensions, needed for the surgeon to reliably and, accurately conduct a given ophthalmic surgery procedure. Movements of the eye are followed by a tracking system which operates at least as fast as both the speed with which the video screen retraces video images and, using dedicated microprocessors, at closed loop refresh speeds greater than several times the maximum repetition rate of the laser. Tracking by following the subject eye tissue, i.e. recognizing new locations of the same tissue and readjusting the imaging system and the surgical laser aim to the new location at total operational speeds faster than the laser firing rate assures that the laser, when firing through a prescribed pattern, will not deviate from the prescribed pattern an unacceptable distance. In preferred embodiments of the invention, this margin of error distance is held within 5 microns in all situations during ophthalmic surgery, although with future use and experimentation it may be found that either more stringent or alternatively more lax error tolerances are desirable to improve overall performance.

In one embodiment of the present invention, a system for use in ophthalmic laser surgery includes a laser source having a beam having power capable of effecting a desired type of surgery in the ocular tissues, with optical path means for delivering the laser beam, including beam directing means for controlling the aim and depth of focus of the laser beam. The system includes three dimensional mapping means for sensing locations, shapes and features on and in a patient's eye in three dimensions, and for generating data and signals in accordance therewith. A display means receives signals from the three dimensional mapping means and presents to a surgeon/user images representative of the locations, shapes and features of the eye in real time. A position analysis means receives signals from the three dimerisional mapping means, and recognizes the occurrence of changes of position of features of the eye, and an associated target tracking means searches for a feature and finds its new position after such a change of position, and generates a signal indicative of the new position. A tracking positioning means receives the signal and executes a change in the aim of the three dimensional mapping means to the new position of a feature in real time, to thereby, follow the feature and stabilize the images on the display means, and simultaneously to adjust the aim of the laser beam to be directed at the new position of the feature targeted.

Figure 16:
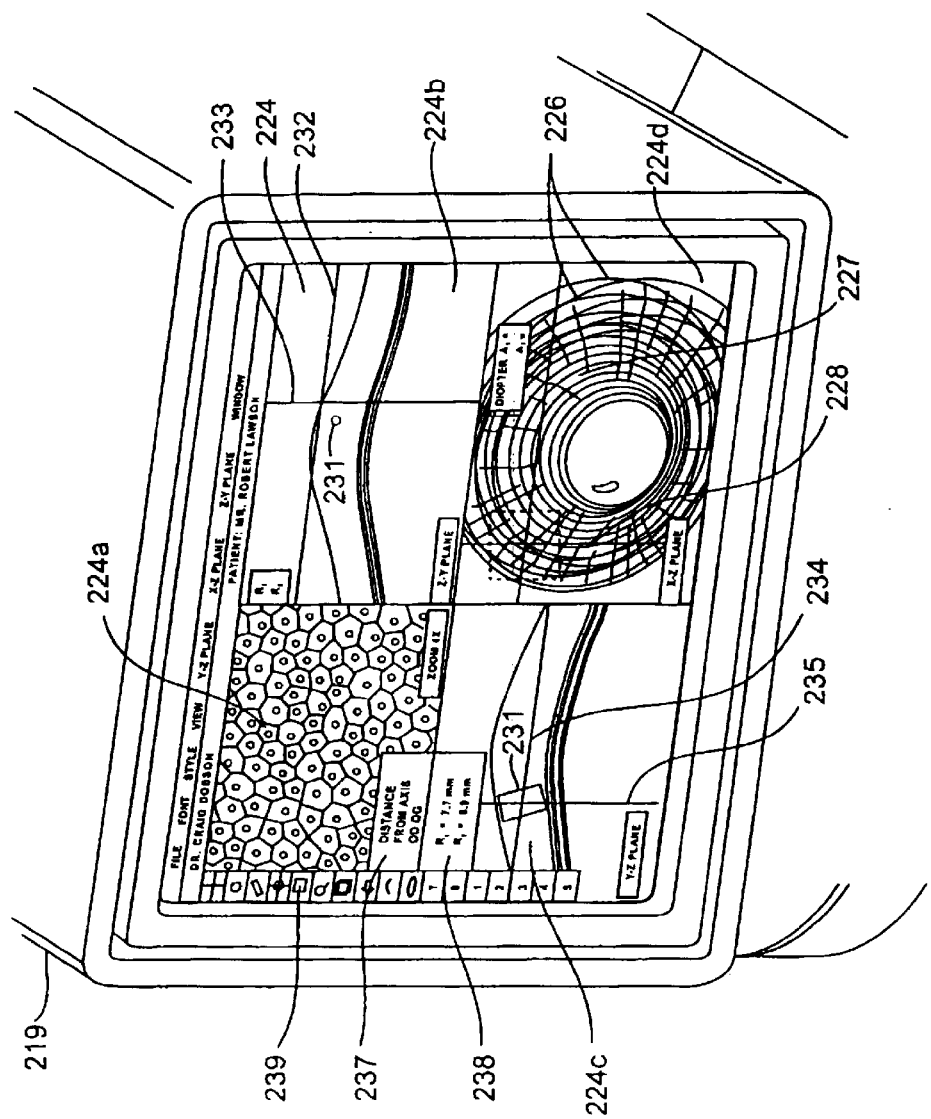
FIG. 16 is an enlarged plan view of a video screen showing an example of information which may be presented to the surgeon/user during the anterior segment ophthalmic surgical procedure.

FIG. 16 shows an example of what may be displayed on a screen 224 of the video monitor 219. The information on the screen 224 is intended to give the user a full range of information regarding the three dimensional structure and features of the particular tissues on which laser surgical procedures are to be performed. For example, the screen may be divided into four quadrants as illustrated. The upper left quadrant 224a may show the image from the video microscope. Thus, individual cell walls may appear in this quadrant as indicated, with relatively high resolution and contrast. These cell walls might be the cells at the inner surface of the cornea, or corneal endothelium. As explained further below, the surgical microscope preferably has a zoom adjustment, so that the magnification power as presented on the screen might vary from about 25.times. to 500.times., as desired by the surgeon/user.

The lower right quadrant 224d of the screen, as illustrated in FIG. 16, can present an enlarged plan view of an area of the patient's tissue, preferably through the full field where the surgical therapeutic treatment is desired. In ophthalmic surgery, this field might comprise, for example, a field of greater dimensions than the cornea for anterior segment procedures, if the surgery is to be conducted in the cornea. For this type of surgery, the plan view or X-Y plane shown in the quadrant 224d may have contour plot with contour levels 226 superimposed concentrically over the image of the cornea. Crosshairs or crossed lines 227 and 228 identify for the surgeon the precise point at which the surgical therapeutic laser is currently directed. These crossed lines may also indicate the line cuts which define the axis for the cross sectional plane representations of the tissue shown in screen quadrants 224b and 224c in FIG. 16. Thus, the crosshairs or crossed lines 227 and 228 in the quadrant 224d indicate planes at which cross sectional representations in the quadrants 224b and 224c are taken. The upper right quadrant 224b shows a cross section along the X-Z plane, taken along the line 227. Similarly, the lower left quadrant 224c of the screen represents the Y-Z plane along the crossed line 228 shown in the quadrant 224d.

The above described preferred embodiments are intended to illustrate the principles of the invention but without limiting its scope. Other embodiments and variations to these preferred embodiments will be apparent to those skilled in the art and may be made without departing from the essence and scope of the invention as defined in the claims.

What is claimed is:

1. A laser surgery system for beating a tissue located at a site of an eye, a real-time image of the tissue at the site being stable as seen by a user, the system comprising:
    a laser for making a beam of a treatment light energy, the treatment light energy being deliverable to the site;
    an imaging system for forming a real-time image of the site and an image of a natural tissue feature, the natural feature being in proximity to the site, the image of the site being visible to the user;
    a detector having the image of the feature formed thereon and generating a first electrical signal in response to the image of the feature formed thereon, the first signal being related to a position of the feature; and
    an electronic device adapted to generate a second electrical sign in response to the first electrical signal, the second signal stabilizing the real-time image of the site as seen by the user as the light energy is delivered to the site.

2. The system of claim 1 wherein the site comprises a moving site and the real-time image comprises a substantially immobilized real-time image of the site as seen by the user.

3. The system of claim 1 wherein the optical system further comprises a movable mirror, and the movable mirror moves in response to the second signal.

4. The system of claim 1 wherein the site is structurally located contiguous to the feature.

5. The system of claim 1 further comprising a display visible to the user, the display showing the stabilized image of the site.

6. The system of claim 5 wherein the image of the site is formed on a camera, the camera being electronically coupled to the display.

7. The system of claim 1 wherein the electronic device comprises an analog circuit for measuring a position of the eye.

8. The system of claim 7 further comprising a display visible to the user, the display showing the stabilized image of the site.

9. The system of claim 8 further comprising at least one processor comprising a computer program adapted to control a delivery of the light energy to the site in response to at least one action of the user.

10. The system of claim 1 wherein the electronic device comprises at least one processor.

11. The system of claim 10 wherein the processor determines a position of the structure from the first signal.

12. The system of claim 10 wherein the at least one processor comprises a computer program adapted to control a delivery of the light energy to the site in response to at least one action of the user.

13. The system of claim 12 further comprising a display visible to the user, the display showing the stabilized image of the site.

14. The system of claim 1 wherein the laser is a pulsed laser.

15. The system of claim 14 wherein a wavelength of the pulsed laser is a non-visible wavelength.

16. The system of claim 15 wherein the laser beam is an ablative light beam for ablation of the tissue structure of the eye.

17. The system of claim 16 wherein the tissue site corresponds to a corneal tissue site of the eye.

18. The system of claim 17 wherein the pulsed laser is an excimer laser.

19. The system of claim 17 wherein the pulsed laser is a solid state laser.

20. The system of claim 17 further comprising:
    optical path means for receiving the short pulse laser beam and for aiming the beam at a point in X-Y directions and focussing the beam at a depth as desired toward a target, including a front lens element from which the beam exits the optical path means toward the patient,
    beam steering means connected to the optical path means for controlling the position at which the beam is aimed in X-Y directions,
    beam focusing means connected to the optical path means for controlling the depth at which the laser beam is focussed,
    tracking means for tracking eye movements of the patient during the progress of the surgery, including X-Y tracking means for tracking a feature of the eye in X and Y directions, and depth or Z tacking means for tracking depth movements of the eye's feature, toward and away from the workstation, and safety interrupt means associated with the processor for interrupting delivery of the laser beam to the patient when it is determined via a processor that the tracking means has lost the feature being tracked.

21. A method of treating a tissue located at a site of an eye of a patient with a laser beam, the treatment sight being stable as seen by a user, the method comprising:

making a beam of a treatment light energy with the laser, the treatment light energy being deliverable to the site;

forming a real-time image of the site and an image of a natural tissue feature with an optical system, the nature feature being in proximity to the site;

measuring a position of the feature from a first electrical signal generated by a detector, the detector having the image of the feature formed thereon, the first signal being related to the position of the feature;

generating a second electrical signal in response to the measured position of the feature, the second signal stabilizing the real-time image of the site as seen by the user; and transmitting the beam of treatment light energy to the treatment site, the second signal stabilizing the real-time image of the site as the treatment light energy is delivered to the site.

22. The method of claim 21 wherein the site comprises a moving site and the real-time image comprises a substantially immobilized real-time image of the site as seen by the user.

23. The method of claim 21 further comprising repeating the steps of measuring the position of the feature and generating the second signal stabilizing the image of the site.

24. The method of claim 21 wherein the second electrical signal comprises an electrical signal generated by a processor.

25. The method of claim 21 further comprising moving a mirror in response to the second signal.

26. The method of claim 25 wherein the step of moving of the mirror results in the real-time image of the site being stable as seen by the user.

27. The method of claim 26 wherein the beam reflects off the mirror.

28. The method of claim 26 wherein the beam is a pulsed laser beam.

29. The method of claim 28 wherein transmitting further comprises ablating a surface of a cornea of the eye.

30. The method of claim 29 wherein the treatment site corresponds to the cornea of the eye.

31. The method of claim 30 further comprising:

receiving the short pulse laser beam and aiming the beam at a point in X-Y directions and focusing the beam at a depth with an optical means and when appropriate toward a target, through a front lens element, controlling the position at which the beam is aimed in X-Y directions, using a beam steering means connected to the optical means, controlling the depth at which the laser beam is focussed, with a bean focussing means connected to tho optical moans, tracking eye movements of the patient during the progress of the surgery in X and Y directions, with an X-Y tracking means for tracking a feature of the eye, and as to depth movements of the eye with a depth or Z tracking means, automatically shifting the optical path means as the feature of the eye is tracked through X-Y and Z movements, so as to change the aim and focus of the laser beam when necessary to follow such movements of the eye, with the aid of a processor connected to the tracking means, and automatically interrupting delivery of the laser beam to the patient when it is determined via the processor that the tracking means has lost the feature being tracked.

32. The method of claim 30 wherein the ablative light beam is an non-visible light beam.

33. The method of claim 32 wherein the laser comprises an excimer laser.

34. The method of claim 33 further comprising ablating the treatment site with a pattern of laser pulses to reshape the cornea to correct a refractive error of the eye.

* * * * *

UNITED STATES PATENT AND TRADEMARK OFFICE
CERTIFICATE OF CORRECTION

PATENT NO. : 6,726,680 B1
DATED : April 27, 2004
INVENTOR(S) : Carl F. Knopp et al.

It is certified that error appears in the above-identified patent and that said Letters Patent is hereby corrected as shown below:

Column 37,
Line 50, delete "beating" and insert therefor -- treating --.
Line 64, delete "sign" and insert therefor -- signal --.

Column 39,
Line 11, delete "nature" and insert therefor -- natural --.

Column 40,
Line 16, delete "bean" and insert therefor -- beam --.
Line 17, delete "moans" and insert therefor -- means --.

Signed and Sealed this

Seventeenth Day of August, 2004

JON W. DUDAS
*Acting Director of the United States Patent and Trademark Office*